(12) United States Patent
Estaquier et al.

(10) Patent No.: US 9,056,071 B2
(45) Date of Patent: Jun. 16, 2015

(54) COMPOUNDS AND METHODS FOR PREVENTING OR TREATING A VIRAL INFECTION

(71) Applicants: INSTITUT NATIONAL DE LA SANTE ET DE LA RECHERCHE MEDICALE (INSERM), Paris (FR); INSTITUT PASTEUR, Paris Cedex 15 (FR); CENTRE NATIONAL DE LA RECHERCHE SCIENTIFIQUE (C.N.R.S.), Paris (FR)

(72) Inventors: Jerome Estaquier, Montmorency (FR); Mireille Laforge, Maisons Alfort (FR); Anna Senik, Paris (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE (C.N.R.S.), Paris (FR); INSTITUT PASTEUR, Paris Cedex (FR); UNIVERSITÉ PARIS-SUD, Orsay (FR)

( * ) Notice: Subject to any disclaimer, the term of this patent is extended or adjusted under 35 U.S.C. 154(b) by 0 days.

(21) Appl. No.: 13/921,998

(22) Filed: Jun. 19, 2013

(65) Prior Publication Data
US 2014/0031276 A1 Jan. 30, 2014

Related U.S. Application Data

(62) Division of application No. 12/740,790, filed as application No. PCT/FR2008/001538 on Oct. 31, 2008, now abandoned.

(30) Foreign Application Priority Data

Nov. 2, 2007 (FR) ..................... 07 07722

(51) Int. Cl.
*A61K 31/47* (2006.01)
*A61K 38/05* (2006.01)
*A61K 38/00* (2006.01)
*A61K 31/404* (2006.01)
*A61K 31/4525* (2006.01)
*A61K 31/496* (2006.01)
*A61K 31/7072* (2006.01)
*A61K 45/06* (2006.01)

(52) U.S. Cl.
CPC ............ *A61K 38/005* (2013.01); *A61K 31/404* (2013.01); *A61K 31/4525* (2013.01); *A61K 31/47* (2013.01); *A61K 31/496* (2013.01); *A61K 31/7072* (2013.01); *A61K 38/05* (2013.01); *A61K 45/06* (2013.01)

(58) Field of Classification Search
CPC . A61K 31/404; A61K 31/4525; A61K 31/47; A61K 38/005
USPC .......................................... 514/4.1
See application file for complete search history.

(56) References Cited

U.S. PATENT DOCUMENTS

| 5,877,197 | A | 3/1999 | Karanewsky et al. |
| 6,184,210 | B1 | 2/2001 | Keana et al. |
| 7,553,852 | B2 | 6/2009 | Knegtel et al. |
| 7,612,091 | B2 | 11/2009 | Charrier et al. |
| 7,829,662 | B2 * | 11/2010 | Korsmeyer et al. ........... 530/300 |
| 2002/0052323 | A1 * | 5/2002 | Wang .............................. 514/19 |

FOREIGN PATENT DOCUMENTS

WO WO 2007/084730 7/2007

OTHER PUBLICATIONS

HIV from Merck Manual, pp. 1-25. Accessed Oct. 8, 2014.*
DeBiasi RL, Robinson BA, Sherry B, Bouchard R, Brown RD, Tizeq M, Long C, Tyler LK, "Caspase Inhibition Protects against Reovirus-induced Myocardial Injury in Vitro and in Vivo," Journal of Virology, 2004, pp. 11040-11050.*
Ulrike Martin et al: "Antiviral effects of pan-caspase inhibitors on the replication of coxsackievirus B3" Apoptosis ; An International Journal on Programmed Cell Death, Kluwer Academic Publishers, BO, vol. 12, No. 3, (Jan. 9, 2007), pp. 525-533.
R. L. Debiasi et al: "Caspase Inhibition Protects against Reovirus-Induced Myocardial Injury in Vitro and in Vivo" Journal of Virology, vol. 78, No. 20, (Oct. 2004), pp .11040-11050.
T. M. Caserta, et al. "Q-VD-OPh, a broad spectrum caspase inhibitor with potent antiapoptotic properties" Apoptosis, vol. 8, 2003, pp. 345-352.
Kleinschmidt Malte C.et al: "Inhibition of apoptosis prevents West Nile virus induced cell death" BMC Microbiology, Biomed Central, London, GB, vol. 7, No. 1, (May 29, 2007), p. 49.
Chiou S-K et al: "Inhibition of ICE-like Proteases Inhibits Apoptosis and Increases Virus Production during Adenovirus Infection", Virology, Academic Press,Orlando, US, vol. 244, No. 1, (Apr. 25, 1998), pp. 108-118.

* cited by examiner

*Primary Examiner* — Julie Ha
(74) *Attorney, Agent, or Firm* — B. Aaron Schulman, Esq.; Stites & Harbison, PLLC

(57) ABSTRACT

A compound is provided which has a structure I: A-B-C and a method for administering the compound is also provided for use in the prophylaxis and/or treatment of a viral infection, and in particular for preventing and/or inhibiting viral replication, in which A is a quinoline or quinoline-like group, B is a sole amino acid or a peptide or polypeptide having a given amino acid sequence, and C is an O-phenoxy group. According to one embodiment, the compound is a protease inhibitor such as a caspase inhibitor, and the inhibitor can be Q-VD-OPh (N-(2-(quinolyl)valylaspartyl-(2,6-difluorophenoxy) methyl ketone), optionally in an O-methylated form. Antiviral compositions and kits are also provided.

28 Claims, 15 Drawing Sheets

COMPOUNDS AND METHODS FOR PREVENTING OR TREATING A VIRAL INFECTION

CROSS-REFERENCE TO RELATED APPLICATION

Figure 1:
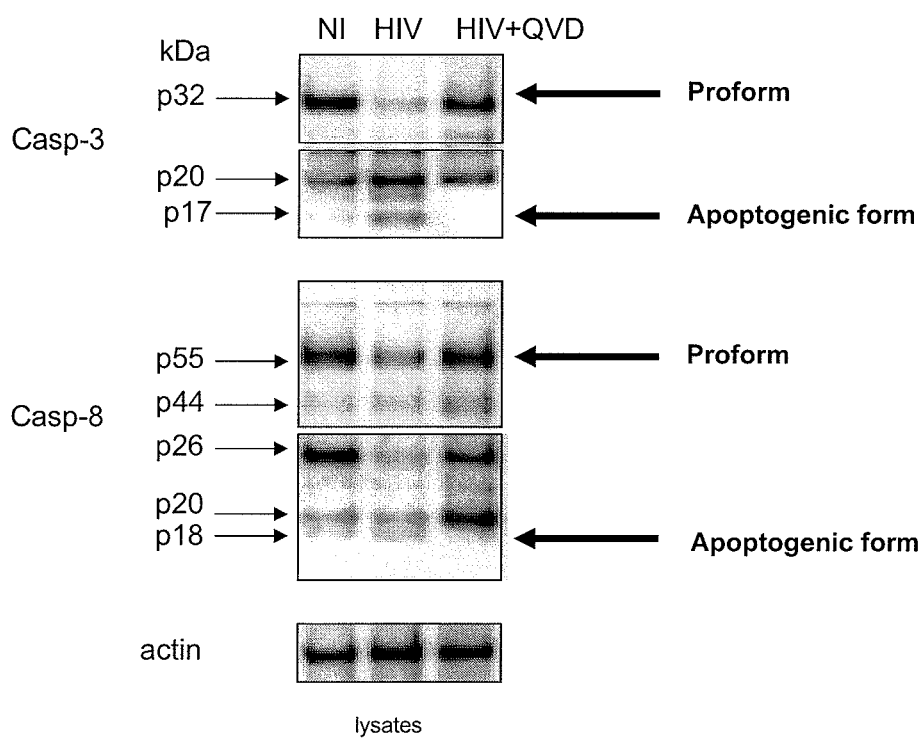

This application is a divisional of U.S. application Ser. No. 12/740,790, having a filing date of Aug. 9, 2010, which is a 371 application of PCT/FR08/01538, filed Oct. 31, 2008, all of said applications incorporated herein by reference.

FIELD OF THE INVENTION

The invention falls within the field of viral infections and the development of novel medicaments for the prophylaxis and/or treatment of viral infections, especially retroviral, in particular lentiviral, infections, for example human immunodeficiency virus (HIV) and simian immunodeficiency virus (SIV) infections.

The invention relates to a compound of structure I: A-B-C, for use in the prophylaxis and/or treatment of a viral infection, in particular for preventing and/or inhibiting viral replication, in which A is a quinoline or quinoline-type group, B is a single amino acid or a peptide or polypeptide having a given amino acid sequence, C is an O-phenoxy group and the symbol "—" indicates that the entities A, B and C are chemically bonded within the compound I.

The invention relates more particularly to the compound Q-VD-OPh (N-(2(quinolyl)valyl-aspartyl-(2,6-difluorophenoxy)methyl ketone), for use in the prophylaxis and/or treatment of a viral infection, in particular for preventing and/or inhibiting viral replication.

The invention relates also to the use of said compound of structure I, and especially of the compound Q-VD-OPh, in the preparation of a pharmaceutical composition for the prophylaxis and/or treatment of a viral infection and, in particular, for preventing and/or inhibiting viral replication.

The present invention relates also to a novel antiviral composition and to a novel combination (or kit) of suitable compounds for use in the prophylaxis and/or treatment of a viral infection, which comprise, consist essentially or consist of:
(i) at least one compound of structure I according to the invention and
(ii) at least one other antiviral agent, for example a viral protease inhibitor or a transcriptase, especially reverse transcriptase, inhibitor.

Finally, the present invention relates to a method for preventing or treating a viral infection in an animal or human.

BACKGROUND OF THE INVENTION

Viral replication is the process by which a virus (DNA or RNA) hijacks and uses the machinery of the cell it infects to multiply. By way of example, the main steps of the replication of retroviruses, and in particular of HIV viruses, are as follows: (1) fixing of the virus to the surface of a cell of an animal or human organism by recognition between virus surface proteins and receptors at the surface of said cell (for example the CD4 receptor); (2) penetration of the virus into the cell cytoplasm by fusion of the virus envelope with the cell membrane; (3) decapsidation of the virus (the virus separates from the matrix and from the capsid, which releases the two copies of the viral genome); (4) reverse transcription of the viral RNAs in the form of a proviral DNA by virtue of reverse transcriptase (viral enzyme); (5) migration of the proviral DNA into the nucleus and integration of that DNA into the DNA of the host cell under the effect of integrase (viral enzyme); (6) transcription of the DNA of the cell into genomic RNA (unspliced messenger RNA (mRNA)) under the effect of the RNA polymerase of the cell; (7) splicing of the mRNA, by excision of the introns, to leave only the exons (which code for the proteins Gag, Pol and Env); (8) translation, in the rough endoplasmic reticulum, of the mRNA in the form of polypeptides; (9) maturation of the polypeptides in the Golgi apparatus, allowing functional polypeptides to be obtained; (10) assembly of the viral particles at the surface of the membrane by accumulation of the multimerized structural polyproteins (Gag, p55), the viral nonstructural proteins (reverse transcriptase, integrase, protease) and the viral RNAs; (11) release of the virions by budding at the surface of the infected cell; and finally (12) maturation of the viruses.

Viruses have developed various strategies for escaping the immune system and facilitating their dissemination during the infection. In particular, the HIV virus has the particular feature of causing the complete breakdown of the immune system by attacking a key cell of the immune system, the auxiliary T lymphocyte (CD4+ T lymphocyte), which expresses at its surface the CD4 molecule, a specific HIV receptor. The monocytes-macrophages, the dendritic cells, the Langerhans cells and the cerebral microglial cells are likewise targets of HIV. The gradual disappearance of the lymphocytes leads to a lack of control of viral replication by the immune system, to the destruction of the lymphoid organs, where the immune response takes place, and to the onset of acquired immunodeficiency syndrome (AIDS), with the occurrence of severe opportunistic infections.

The mechanisms responsible for the disappearance of the CD4+ T lymphocytes during infection by HIV are complex, and they have been elucidated only partially.

The HIV viral particle is composed of a nucleocapsid which contains the single-stranded RNA dimer of positive polarity associated with the nucleocapsid protein, lysine tRNAs and the viral enzymes (reverse transcriptase, protease and integrase). The nucleocapsid is enclosed in a coat of matrix proteins which is covered by a lipid membrane borrowed from the host cell during budding of the viral particle. The membrane is provided with spikes composed of envelope glycoprotein oligomers. The step of conversion of the RNA into bicatenary DNA during the viral cycle under the action of a viral enzyme, reverse transcriptase, is the main characteristic of the retroviruses.

The viral genes gag, pol and env are retained in all retroviruses. All the products derived therefrom are present in the viral particle. They come from the cleavage of precursor polyproteins. The genes gag and env code for structural proteins, and the gene pol codes for numerous enzymatic proteins.

The Gag proteins are obtained from the cleavage of the polyprotein Pr55gag by viral protease. The cleavage releases the matrix protein, the capsid protein, the nucleocapsid protein, as well as a 6 kDa protein. Recent works suggest that these processes play an essential role in the genesis of infectious viral particles (Sticht et al., 2005; Ternois et al., 2005). These recent works have made it possible to generate, for the first time, an HIV assembly inhibitor.

The envelope precursor gp160 is cleaved into a surface glycoprotein gp120 (gp130 for SIVmac) and a transmembrane protein gp41 derived from the C-terminal region of the precursor. During its maturation, the precursor gp160 is glycosylated and then cleaved by a cell protease in the Golgi apparatus and then exported to the plasmic membrane. The two glycoproteins derived from the cleavage remain associated by non-covalent bonds. They form heteromers of envelope glycoproteins, which combine in oligomers to form the spikes of the virion.

The invention relates more particularly to the compound Q-VD-OPh (N-(2-quinolvl)valyl-aspartyl-(2,6-difluorophenoxy)Methyl ketone), for use in the prophylaxis and/or treatment of a viral infection, in particular for preventing and/or inhibiting viral replication.

Reverse transcriptase is derived from the cleavage of the polyprotein Pr160gag-pol in two steps by the viral protease during the assembly of the viral particle.

Located in the C-terminal position of the Pol region of the polyprotein Gag-Pol, integrase is released in the form of a 32 kDa protein under the action of the viral protease. Its oligomerization is required both for its incorporation into the viral particle and to exert its activity of integrating linear double-stranded viral DNA into the cell genome.

All of these works emphasize the major role of protease(s) in the genesis of an infectious viral particle. Accordingly, as well as using retrotranscriptase inhibitors or nucleoside analogues, the HIV therapy known as highly active anti-retroviral therapy or "HAART" today includes one or more HIV protease inhibitors. This therapy leads to inhibition of viral replication, an increase in the number of CD4 T lymphocytes and an indisputable clinical improvement.

However, in so far as no current treatment enables patients to be cured of AIDS, and HIV virus isolates are or are becoming resistant to existing treatments, it is necessary to find other antiviral molecules which allow viral infections in general and infections by retroviruses such as HIV in particular to be combated more effectively.

Many viral infections coincide with disturbances in the mechanisms that control cell death (Barber, 2001). In particular, many works indicate that there is a relationship between in vitro or in vivo infection by HIV and an increase in the susceptibility to apoptosis of the T lymphocytes. Apoptosis (or programmed cell death or even cell suicide) is the process by which cells trigger their self-destruction in response to a signal (pro-apoptotic signal). The environment, interactions between cells, the absence of nourishment for the cell, infection by a pathogenic agent, are a few examples of proapoptotic signals. Apoptosis is a morphologically and biochemically defined form of cell death which is characterized in vivo by the absence of an inflammatory response, the activation of caspases and the cleavage of numerous proteins, fragmentation of the DNA, condensation of chromatin, cell contraction and the disassembly of cell structures to form vesicles incorporated into the membrane (apoptotic bodies). In vivo, this process culminates in the phagocytosis of apoptotic bodies by other cells.

Precocious apoptosis of a cell infected by a virus can constitute a defence mechanism of the host; it allows the number of viral particles released to be limited by interrupting viral replication. The cell endonucleases produced during apoptosis can act on the viral DNA and inhibit the synthesis of viral, structural and regulatory proteins and the formation of infectious viral particles, thus limiting the dissemination of virions in the host.

Accordingly, many viruses act on the regulation of the apoptotic intracellular signals, either in order to keep themselves alive or to keep the infected cell viable or to prevent the cell from being attacked by the effector cells of the immune system, and thus increase the efficacy of viral replication and permit greater production of virions. The majority of viruses have one or more genes permitting the synthesis of proteins whose effect is to suppress, at different stages, apoptosis of the cells they infect (antiapoptotic proteins). By retarding or inhibiting the death of the host cell, viruses promote the survival of the cell they infect and therefore their own survival, to the extent of promoting the occurrence of cancers in some cases.

Other viruses, on the other hand, have also developed strategies for causing the death of the cells they infect, leading to cell deficiencies, in particular immune deficiencies (such as those associated with AIDS), neuronal deficiencies (such as those associated with rabies) and epithelial deficiencies (such as those associated with haemorrhagic fevers). In the case of immune deficiencies alone, the viruses are then able to propagate. Some viruses are additionally capable of inducing apoptosis at a late phase of the infection, which allows the virions to propagate into the neighbouring cells while escaping the inflammatory and immune response of the host (Everett & McFadden, 1999).

The apoptotic processes induced by viruses are at the origin of cell disturbances which influence the clinical evolution of viral infections. Infection by HIV is a very representative example. Infection by HIV-1 is accompanied by abnormal induction of apoptosis in the adult T lymphocytes, the thymocytes and the haematopoietic precursors. Moreover, in a large number of patients, excess apoptosis affects all the lymphocyte populations (CD4 T, CD8 T and B), and the degree of apoptosis correlates with the evolution of the disease (Gougeon et al., 1996). In addition, in some patients infected by HIV, lymphocyte apoptosis is abnormally elevated in the lymphatic ganglions (Amendola et al., 1996), which constitute the main replication sites of the virus. Most surprising is that, in patients infected by HIV, the majority of the T cells that undergo apoptosis are not infected by the virus ("bystander" effect) (Finkel et al., 1995). These observations suggest that the destruction of the lymphocytes by HIV is the result of the activation by the virus of cytopathogenic mechanisms which are both direct and indirect.

The regulation of apoptosis by HIV is all the more complex because the virus is capable of manipulating the apoptotic machinery to its advantage by acting as both an activator and a repressor of apoptosis. HIV has in fact also developed mechanisms of inhibiting apoptosis in order to escape the host's immune system.

Various studies have shown that other lentiviruses, in particular feline immunodeficiency virus (FIV) and some strains of simian immunodeficiency virus (SIV), are also capable of inducing apoptosis and causing an immune deficiency syndrome in their natural host. Accordingly, within the scope of a study of different models of chronic lentiviral infections in primates, the inventors of the present invention have previously shown that the CD4+ T lymphocytes are abnormally sensitive to apoptosis in the rhesus macaque infected by the pathogenic strain SIVmac251 (Hurtrel et al., 2005).

On the other hand, in models of chronic lentiviral infections of primates in which the infection, whatever the lentiviral isolate in question, does not cause AIDS (chimpanzees experimentally infected by HIV, African green monkeys naturally infected by SIVagm), there is no abnormal programming of apoptosis of the CD4+ T lymphocytes in vitro. However, this absence of disease is not linked to the absence of pathogenic potential of the virus, since these viruses are capable of inducing AIDS in macaques (Hurtrel et al., 2005). Accordingly, these models of lentiviral infections underline the importance of factors proper to the host, which will determine either the occurrence of apoptosis associated with the development of AIDS, or the absence of pathology.

One of the major components of the machinery of apoptosis is a family of cysteine proteases called caspases (from the English cysteinyl aspartate-specific proteases or cysteine aspartate proteases). Caspases have been found in many organisms, ranging from *C. elegans* to humans. To date, more than about twelve caspases have been identified. These intracellular enzymes have a key role in apoptosis, inflammation, activation and cell differentiation.

Like other proteases, caspases are expressed in the form of proenzymes which undergo proteolytic maturation. These precursors are expressed constitutively in the cell cytoplasm. The procaspases (from 30 to 50 kD) contain three domains: an N-terminal prodomain, a large subunit (about 20 kD) and a small subunit (about 10 kD). Activation involves proteolytic cleavage between the domains, followed by the association of the large and the small subunit, each of which contributes to the amino acids of the active site, to form a heterodimer. The active mature enzymes function in the form of a tetramer composed of two heterodimers. The N-terminal domain of the caspases, whose length (from 23 to 216 amino acids) and sequence vary greatly, is involved in the regulation of those enzymes.

The function of the caspases is determined by their substrate specificity, the length of their prodomain and the sequence of the prodomain. The caspases can be divided into three groups: the inflammatory caspases (group I), the initiator (or regulatory) caspases (group II) and the effector (or executor) caspases (group III) (Lavrik et al., 2005). The long prodomain (more than 100 amino acids) of the initiator caspases and of the inflammatory caspases acts as an apoptotic or proinflammatory signal integrator. The inflammatory caspases include caspase-1, -4, -5, -11, -12, -13 and -14. They are involved in the inflammatory processes and play a central role in the activation of certain cytokines. The initiator caspases include caspase-2, -8, -9 and -10. They are located upstream of the apoptotic signalling cascades and are activated by autoproteolytic mechanisms in response to proapoptotic signals. They then cleave and activate the effector caspases, which are located downstream of the signalling cascades, permitting amplification of the apoptotic signal. The effector caspases include caspase-3, -6 and -7. They are involved directly in the execution or occurrence of apoptosis; once activated by the initiator caspases, they cleave numerous cell proteins, thus leading to dismantling of the cell or inactivation of other proteins (Thornberry and Labzebnik, 1998). The proteins inactivated by the action of these caspases (approximately from 2000 to 3000 substrates) include proteins which protect the cells from apoptosis (antiapoptotic proteins), such as proteins of the Bcl-2 family.

The caspases, the catalytic domain of which includes a cysteine residue (C), cleave their protein substrate(s) at specific consensus sites containing an aspartic residue which are located in the carboxy-terminal part of the substrate. They exhibit substrate recognition motifs and highly conserved catalytic motifs (Cryns et al., 1998).

The preferences or substrate specificities of individual caspases have been used to develop peptides which effectively enter into competition with the binding of the caspases to their substrate. Such synthetic inhibitors are now available commercially. Some broad-spectrum caspase inhibitors include a single amino acid or a generally di- to tetra-peptide amino acid sequence, which is optionally O-methylated and which is conjugated to a carboxy-terminal group such as fluoromethyl ketone (fmk), chloromethyl ketone (cmk), an aldehyde group (CHO) or a difluorophenoxy group (OPh). Such inhibitors have been described especially in patent application WO 02/183341. These caspase inhibitors are capable of penetrating the cells and binding irreversibly (with the exception of inhibitors having an aldehyde group, whose binding is reversible) to the active site of the caspases. They accordingly act as proteolytic decoys by blocking proteolytic caspase cleavage, which is required for activation of said caspases and the production of an active truncated caspase. Inhibitors having a carboxy-terminal group fmk or OPh have been formulated for in vivo and in vitro applications.

Two of the most widely used caspase peptide inhibitors are the inhibitors Boc-D-fmk (tert-butyloxycarbonyl-Asp(O-methyl)-fluoromethyl ketone; Enzyme Systems Products, CalBiochem or R&D Systems) and z-VAD-fmk (N-benzyloxycarbonyl-Val-Ala-Asp-fluoromethyl ketone; Enzyme Systems Products, CalBiochem or R&D Systems). The Boc (tert-butyloxycarbonyl) and z (N-benzyloxycarbonyl) groups serve to block the amino acid sequences D (Asp) or VAD (Val-Ala-Asp), while the fluoromethyl ketone group in the carboxy-terminal position facilitates membrane permeability. It has been shown that inhibition of the activation of caspases by such inhibitors prevents the appearance of the morphological modifications which are characteristic of apoptosis (Chinnaiyan et al., 1997).

A more recently developed caspase inhibitor, Q-VD-OPh (N-(2-quinolvl)valyl-aspartyl-(2,6-difluorophenox)methyl ketone; Enzyme Systems Products, CalBiochem or R&D Systems), has increased efficacy, stability and permeability as compared with inhibitors having a carboxy-terminal group of the fluoromethyl ketone (fmk) type, and reduced toxicity, even when used in a high concentration; this inhibitor has been found to be non-toxic at doses of up to 1 g/kg live weight, when administered to mice by the intraperitoneal route (Vera et al., 2005).

The inhibitor Q-VD-OPh has been found to be functional in vitro, in different cell types, and in vivo, in animal models, in particular in the mouse and the rat. Moreover, it has been shown that it inhibits various caspases, in particular caspase-1, -3, -8, -9, -10 and -12, with IC50 values ranging from 25 to 400 nM. Furthermore, Q-VD-OPh, like the inhibitors ZVAD-fmk and Boc-D-fmk, inhibits apoptosis in a dose-dependent manner (Caserta et al., 2003).

It has been proposed that the inhibition of caspases or the overexpression of the antiapoptotic protein Bcl-2 might prevent viral infections by inhibiting apoptosis, and also disrupt viral production (Levine, 1996; Olsen, 1996; Liang, 1998; Wurzer, 2003). However, studies conducted in vitro using the caspase inhibitor z-VAD-fmk did not enable viral replication to be inhibited (Gandhi et al., 1998; Petit et al., 2002). On the contrary, administration of the caspase inhibitor z-VAD-fmk to T-leukaemia cells (CEM) or to peripheral blood mononuclear cells (PBMC) exposed to the HIV-1 virus had the effect of increasing viral replication (Chinnaiyan et al., 1997). Similar results have been observed in the case of CEM cells expressing the CrmA (cytokine response modifier A) protein of the vaccinia virus, a viral caspase inhibitor that inhibits especially activation of caspase-1, -6 and -8 (Chinnaiyan et al., 1997). This suggests that the results observed in the case of the inhibitor z-VAD-fmk are not specific to that inhibitor but rather the result of the inhibition of proapoptotic proteases. Furthermore, the inhibitor z-VAD-fmk is capable of stimulating endogenous viral replication in activated PBMCs derived from patients who are HIV-1-positive but are asymptomatic (Chinnaiyan et al., 1997). The totality of these results suggests that apoptosis might help the host to limit propagation of the virus and that, consequently, strategies aimed at inhibiting cell death might have deleterious consequences for the infected host and might, in particular, contribute towards increasing the viral load of an HIV-positive individual. This would be in agreement with the fact that many viruses produce proteins that inhibit cell death in the host (for example the CrmA protein produced by the vaccinia virus).

SUMMARY OF THE INVENTION

In view of these earlier results, the present invention appears surprising. The results presented in the present application in fact show that the compound Q-VD-OPh not only permits inhibition of the apoptotic phenotype (caspase inhibition, DNA condensation and fragmentation) of the HIV-infected cells, but also inhibition of their death and especially inhibition of viral replication.

The invention accordingly relates to the compound Q-VD-OPh or a derivative thereof and, more generally, to a structure I as defined in the present application, for use as a medicament, in particular as an antiviral agent and more particularly as an antiretroviral agent. Said compound is used in particular for the prophylaxis and/or treatment of a viral infection, in particular in an animal or human, and more particularly for inhibiting viral replication in an animal or human infected by a virus.

The invention relates also to the use of at least one compound of structure I, in particular to the use of the compound Q-VD-OPh, in the preparation of a pharmaceutical composition for the prophylaxis and/or treatment of a viral infection, in particular in an animal or human, and more particularly for preventing and/or inhibiting viral replication in an animal or human infected by a virus.

DETAILED DESCRIPTION OF THE PREFERRED EMBODIMENTS

Unless indicated otherwise, each embodiment indicated in this application applies independently and/or in combination with the other embodiments described.

Said compound I comprises or consists of at least one amino acid, that is to say a single amino acid or a plurality of amino acids in the form of a peptide or polypeptide having a given amino acid sequence, the carboxyl group of said single amino acid or the C-terminal portion of said peptide or polypeptide being bonded to an O-phenoxy group and the amine group of said single amino acid or the N-terminal end of said peptide or polypeptide being bonded to a quinoline or quinoline-type group. It has been shown that the use of carboxy-terminal O-phenoxy groups enables the efficacy of caspase inhibitors to be improved and their toxicity to be reduced (Caserta et al., 2003).

In other words, the compound of structure I is of the type A-B-C, A being a quinoline or quinoline-type group, B being a single amino acid or a peptide or polypeptide having a given amino acid sequence, and C being an O-phenoxy group, the symbol "-" indicating that the entities A, B and C are chemically bonded within the compound I. According to a particular embodiment, the groups A, B and C are bonded (or fused) covalently, for example by way of peptide bonds.

The term "quinoline" as used in the present application includes the structure of the 1-aza-naphthalene type.

The expression "quinoline-type" as used in the present application includes structures having a carbonyl group fixed in the 2- or 3-position to the quinoline, in particular to the 1-aza-naphthalene structure, for example quininic acid. This expression also includes the melatonin structure and similar structures. According to a particular embodiment, said quinoline-type group is the group 2-quinolylcarbonyl.

In a particular embodiment, the quinoline group is replaced by the indole structure. The expression "quinoline-type" then includes structures having a carbonyl group fixed in the 2- or 3-position to the indole structure.

In a particular embodiment, the structure I is:

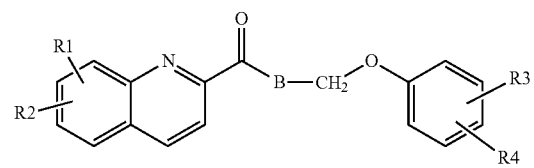

in which

B is a single amino acid or a peptide or polypeptide having a given amino acid sequence, R1 and R2 are selected from a hydrogen, an alkyl, an alkoxy, a fluoro, a chloro, a carboxy, a carbonyl, an arylcarbonyl and an amino, and R3 and R4 are selected from a hydrogen, an alkyl, an alkoxy, a fluoro, a chloro, a carboxy, a carbonyl, an arylcarbonyl and an amino.

As used in the present application, the term "alkyl" refers to alkyl groups having preferably from approximately 1 to 20 carbon atoms, more preferably from approximately 1 to 10 carbon atoms, for example 1, 2, 3, 4, 5, 6, 7, 8, 9 or 10 carbon atoms. The term includes all the configurations of the alkyl groups. According to a particular embodiment, said alkyl group is a methyl group or an ethyl group.

As used in the present application, the term "alkoxy" or "alkoxyl" denotes the group —O-alkyl having preferably from approximately 1 to 20 carbon atoms, more preferably from approximately 1 to 10 carbon atoms, for example 1, 2, 3, 4, 5, 6, 7, 8, 9 or 10 carbon atoms. These terms include all the configurations of the alkyl groups. According to a particular embodiment, said alkyl group is a methyl group or an ethyl group.

The term "aryl" includes especially the groups phenyl, naphthalyl and similar structures.

The expression "peptide or polypeptide having a given amino acid sequence" as used in the present application denotes a chain of several (at least two) successive amino acids forming the structure of a peptide (that is to say a chain of less than 20 amino acids) or of a polypeptide (that is to say a chain of more than 20 amino acids).

According to a particular embodiment, the peptide has a di-, tri- or tetra-peptide sequence, that is to say a sequence composed of two, three or four successive amino acids.

According to a particular embodiment, the single amino acid is an aspartic acid (D or Asp) or said peptide or polypeptide comprises at least one aspartic acid.

According to a particular embodiment, the compound of structure I comprises an aspartic acid (D) and a valine (V or Val). By way of example, when said peptide or polypeptide has a dipeptide sequence, its sequence can be Valine-Aspartic acid (VD). In the case of a tripeptide peptide or polypeptide, its sequence can be Valine-X-Aspartic acid (VXD) or Valine-Aspartic acid-Alanine (VD, for example Valine-Alanine-Aspartic acid (VAD).

According to a particular embodiment, part B of the compound of structure I comprises or consists of the chain of amino acids Valine-Aspartic acid (VD). When it comprises other residues, said chain can be followed and/or preceded by one or more (two, three, four, five or more than five) other amino acid(s), which can be of any type.

According to a particular embodiment, the compound of structure I is A-VD-C, in which A and C have any one of the definitions given in the present application, and more particularly the compound Q-VD-OPh.

According to a particular embodiment, the invention does not relate to the compound Q-DEVD-OPH and/or to the compound Q-LEDH-OPH and/or to the compound Q-IETD-OPH, taken as such.

According to a first embodiment, the single amino acid or at least one of the amino acids of the peptide or polypeptide of the compound of structure I is O-methylated. When the single amino acid is an aspartic acid or when the peptide or polypeptide comprises at least one aspartic acid, said compound can in particular be O-methylated on the aspartic acid or on at least one of its aspartic acids.

According to a second embodiment, the single amino acid or the amino acid sequence of the peptide or polypeptide of the compound of structure I is not O-methylated. The absence of O-methylation is supposed to reduce the hydrophobicity of the peptide and facilitate its use in an aqueous medium.

According to a particular embodiment, R1 and/or R2 is(are) hydrogen.

According to a particular embodiment, R3 and/or R4 is(are) a fluoro.

According to a particular embodiment, the compound of structure I according to the invention is a protease inhibitor, in particular a caspase inhibitor.

In the present application, the term "caspase" denotes any cysteine protease as defined above.

"Protease inhibitor" or "caspase inhibitor" is understood as meaning any compound which is capable of inhibiting the activation of at least one protease or the activation of at least one caspase, respectively, in particular any compound which prevents or inhibits the process of proteolytic cleavage which allows said protease or caspase to be obtained in active form. In particular, said caspase inhibitor prevents or inhibits the production of apoptogenic forms of the caspase in question. Demonstration of the inhibition (of the activation) of one or more protease(s) and in particular of one or more caspases can be carried out, for example, by immunotransfer (Western blot) using antibodies specific for different forms and proforms of said protease(s) or caspase(s) which are supposed to be inhibited by said inhibitor, as described in FIG. 1 and in Example B-1. The inhibition of one or more protease(s) or caspase(s) can be total (in which case the active form of said protease(s) or caspase(s) is not detected) or only partial (said protease(s) or caspase(s) is(are) then detected in active form but in a reduced quantity as compared with the quantity detected in the absence of the inhibitor).

According to a particular embodiment, the compound of structure I according to the invention inhibits:
  at least one caspase selected from the inflammatory caspases (group I), in particular caspase-1, -4, -5, -11, -12, -13 and -14, more particularly caspase-1 and -12; and/or
  at least one caspase selected from the initiator caspases (group II), in particular caspase-2, -8, -9 and -10, more particularly caspase-8 and -10; and/or
  at least one caspase selected from the effector caspases (group III), in particular caspase-3, -6 and -7, more particularly caspase-3.

According to a particular embodiment, the compound of structure I inhibits a plurality of caspases (two, three, four or more than four caspases) of group I and/or of group II and/or of group III.

According to a particular embodiment, the compound of structure I according to the invention is a broad-spectrum inhibitor, that is to say it inhibits one or more caspase(s) from two groups selected from groups I, II and III or from the three groups I, II and III.

According to a particular embodiment of the invention, the compound of structure I according to the invention or one of the compounds of structure I according to the invention is the compound of the following formula:

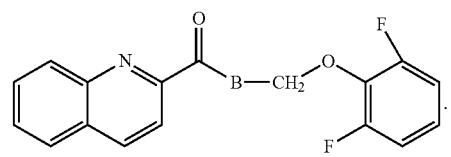

According to a particular embodiment of the invention, the compound of structure I according to the invention or one of the compounds of structure I according to the invention is the O-methylated compound Q-VD-OPh (N-(2-quinolyl)valyl-O-methyl-aspartyl-(2,6-difluorophenoxy)methyl ketone), the empirical formula of which is C27H27F2N3O6, or the non-O-methylated compound Q-VD-OPh (N-(2-(quinolyl)valyl-aspartyl-(2,6-difluorophenoxy)methyl ketone), the empirical formula of which is C26H25F2N3O6. According to a particular embodiment of the invention, therefore, the compound of structure I according to the invention or one of the compounds of structure I according to the invention is the compound of the following formula:

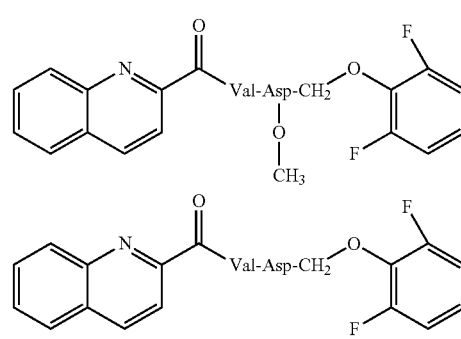

The compound Q-VD-OPh is preferably in O-methylated form, the non-O-methylated form generally being less stable than the O-methylated form.

In the present application, "antiviral agent" and "antiretroviral agent" are understood as meaning, respectively, any agent (that is to say any active ingredient) having an antiviral or antiretroviral effect. Such agents include in particular antiviral and in particular antiretroviral medicaments which act on at least one step of the replication of the virus. In particular, said agents can allow viral replication to be prevented, reduced or inhibited.

The present invention relates also to a composition, in particular a pharmaceutical composition, comprising at least one compound of structure I as defined in the present application.

Accordingly, the compound according to the invention, which is used in the prophylaxis and/or treatment of a viral infection, can be characterized in that it is used in the production of a composition, in particular a pharmaceutical composition (for example an antiviral composition). Where appropriate, said composition further comprises one or more carrier(s), diluent(s) or adjuvant(s) or a combination thereof.

The compound of structure I according to the invention, like a composition (in particular a pharmaceutical composition) or a combination (or kit) comprising said compound of structure I (see hereinbelow), can be administered to any animal or human likely to benefit from such administration, in particular to any animal or human infected or likely to be infected by a virus as described in the present application.

As used in the present application, the term "animal" defines any non-human animal, in particular any non-human mammal, and more particularly an ape or a cat.

As used in the present application, the expressions "viral infection" and "infected by a virus" mean that said animal or human has been exposed to a pathogenic RNA or DNA virus and that said virus has attached itself to one or more cells of the host and has then penetrated (or is likely to penetrate) into said cell(s) and has had (or will possibly have) harmful effects for at least one cell of said animal or human. In particular, such a viral infection is capable of evolving into clinical signs of induced pathologies or pathologies accompanying said infection. Accordingly, a "viral infection" within the scope of the present invention includes the earliest phases of viral contamination as well as the latest phases and the intermediate phases of viral contamination. By way of example, in the case of HIV, the infection evolves in several phases which may follow one another over time. Four phases in particular are distinguished: (1) the primary infection corresponds to the phase of seroconversion which follows contamination and is (in 50 to 75% of cases) or is not accompanied by symptoms; it is followed by (2) a latent phase, then (3) a phase with minor symptoms, and finally (4) the phase of profound immunodepression or the AIDS stage, which is generally symptomatic and is generally accompanied by numerous opportunistic infections.

The term "viral infection" therefore also includes any clinical sign, symptom or disease that occurs in an animal or human (patient) following contamination of said animal or patient by a virus as described in the present application. Accordingly, the "viral infection" includes both contamination by said virus and the various pathologies which are the consequence of contamination by said virus.

The viral infections which fall within the scope of the present invention include in particular the group constituted by viral encephalitis, viral meningitis, aphthous fever, influenza, yellow fever, respiratory viral infections, infantile diarrhea, in particular infantile diarrhea caused by rotavirus, haemorrhagic fevers, in particular haemorrhagic fevers caused by the Ebola virus, the dengue virus and the Lassa virus, poliomyelitis, rabies, measles, rubella, varicella, smallpox, herpes zoster, genital herpes, hepatitis, especially A, B, C, D and E, SARS, leukaemia and paralysis due to HTLV-1 (human T lymphotropic virus type 1), as well as infections caused by an HIV virus, and more particularly by HIV-1 or HIV-2, or an SIV virus, which include in particular acquired immunodeficiency syndrome (AIDS).

The term "prophylaxis" denotes any degree of retardation in the time of appearance of clinical signs or symptoms of the viral infection, as well as any degree of inhibition of the severity of the clinical signs or symptoms of the viral infection, including, but not being limited to, the total prevention of the viral infection. This requires the compound of structure I according to the invention or the composition or combination comprising said compound of structure I to be administered to the animal or patient likely to be contaminated by a virus before any clinical sign or symptom of the disease appears. The prophylactic administration of the compound of structure I according to the present invention or of a composition or combination comprising said compound can take place before said animal or human is exposed to the virus responsible for the viral infection, or at the time of exposure. Such a prophylactic administration serves to prevent and/or reduce the severity of any subsequent infection.

The above definition of the term "prophylaxis" also applies to the expression "prevent an infection".

"Treatment" is understood as meaning the therapeutic effect produced on an animal or human by the active substances (in particular the caspase inhibitor(s) according to the invention) when they are administered to said animal or human at the time of contamination of said animal or human by the virus or after contamination. When the compound of structure I according to the invention or a composition or combination comprising said compound of structure I is administered to an animal or human after contamination by the virus, it can be administered during the primary infection phase, during the asymptomatic phase or after the appearance of clinical signs or symptoms of the disease. According to a particular embodiment, administration takes place within 24 or 48 hours of said animal or human being exposed to said virus, as quickly as possible.

The term "treatment" includes any curative effect obtained by virtue of the compound of structure I according to the invention or a composition or combination comprising said compound, and also the improvement in the clinical signs or symptoms observed in the animal or patient as well as the improvement in the condition of the animal or patient. The term includes in particular the effects obtained as a consequence of inhibiting viral replication and/or inhibiting cell death induced by the virus. Accordingly, the term "treatment" covers the slowing down, reduction, interruption and stopping of the viral infection and/or of the harmful consequences of the viral infection; treatment does not necessarily require the complete removal of all the clinical signs of the viral infection and the symptoms of the disease, nor the complete elimination of the virus.

The definition of the term "treatment" also applies to the expression "treat an infection".

The compound of structure I according to the invention or a composition or combination comprising said compound of structure I can therefore be administered to an animal or human at risk of developing a viral infection (prophylaxis) or after contamination by the virus has taken place, in particular after manifestation of the first clinical signs or symptoms of the disease, for example after proteins or antibodies specific to said virus have been detected in the blood of the animal or patient (treatment). According to a particular embodiment, treatment is started when the patient exhibits clinical signs of immunodepression or when the level of T lymphocytes, in particular TCD4+ lymphocytes, in a sample of blood taken from the patient or animal is less than 350 per microlitre, in particular less than 200 per microlitre.

According to a particular embodiment, therefore, the compound of structure I according to the invention or a composition or combination comprising said compound of structure I is administered to an animal or human before said animal or human is exposed to said virus, during exposure to said virus or after exposure to said virus. Administration after exposure to the virus can be carried out at any time but will preferably be carried out as quickly as possible after exposure, in particular within 48 hours of the animal or human being exposed to said virus.

Furthermore, it is also possible to envisage a plurality of successive administrations of the compound of structure I according to the invention or of a composition or combination comprising said compound, so as to increase the beneficial effects of the treatment. In order to increase the chances of cure, or at least prolong the life expectancy of the animal or human, or the prophylactic effect, it is possible in particular to carry out one or more successive administrations of said compound of structure I or of said composition or combination or of said kit before the animal or human is exposed to the virus and/or during exposure to the virus and/or after exposure to the virus, in particular within 48 hours of said animal or human being exposed to said virus.

The viruses that fall within the scope of the present invention include DNA viruses and RNA viruses, in particular viruses responsible for cell deficiencies such as immune deficiencies (such as AIDS), neuronal deficiencies (such as rabies) or epithelial deficiencies (such as haemorrhagic fevers).

More specifically, said virus is a virus selected from the following families:
- the flaviviridae, in particular those of the genus flavivirus, which includes especially the dengue virus, the yellow fever virus and the viruses responsible for viral encephalitises, such as the West Nile virus, the Japanese encephalitis virus and the Saint-Louis encephalitis virus;
- the orthomyxoviruses, which include the influenza viruses;
- the paramyxoviridae, in particular those of the genus morbillivirus, especially the measles virus, and the respiratory viruses, in particular those of the genus pneumovirus, for example human respiratory syncytial virus and metapneumovirus;
- the reoviridae, in particular the virus of the genus rotavirus;
- the picornaviridae, in particular the viruses of the genus enterovirus, including the polioviruses and the viruses responsible for viral meningitis, those of the genus aphthovirus, especially the aphthous fever virus, and those of the genus rhinovirus;
- the filoviridae, in particular the Ebola virus;
- the arenaviridae, in particular the Lassa virus;
- the rhabdoviridae, in particular those of the genus rhabdovirus, including the rabies virus, and the genus vesiculovirus, which includes the vesicular stomatitis virus;
- the togaviridae, in particular of the genus Rubivirus, including the rubella virus;
- the poxyiridae, in particular the vaccinia and variola viruses;
- the herpesviridae, in particular the Herpes, varicella and Zoster viruses;
- the hepatitis viruses, especially the hepatitis A, B, C, D and E viruses;
- the coronaviridae, in particular the genus coronavirus, for example the SARS virus;
- the retroviruses, in particular those of the genus lentivirus and those of the genus oncovirus, for example the HTLV-1 virus.

The present invention is directed in particular to the lentiviruses, in so far as they cause the degeneration of multiple organs.

According to a particular embodiment, said virus is a human retrovirus, in particular a human lentivirus, more particularly a human immunodeficiency (HIV) virus such as HIV-1 or HIV-2, and preferably HIV-1.

According to another particular embodiment, said virus is a simian retrovirus, in particular a simian lentivirus, and more particularly a simian immunodeficiency virus (SIV) such as the SIVmac251 or SIVmac239 virus or any other virus mentioned in Gordon et al.

The compound(s) of structure I according to the invention or a composition or combination comprising the compound(s) of structure I can be used to prevent, reduce and/or inhibit viral replication in an animal or human infected by a virus as defined above.

The term "viral replication" as used in the present application includes the totality of the steps of the replication cycle of the virus, in particular the main steps of replication of the retroviruses described in the present application, including entry of the virus into the cell, integration of the viral genome into the DNA of the host cell, and viral maturation.

"Viral maturation" or "maturation of the viruses" denotes, in the case of the lentiviruses and in particular in the case of the HIV viruses, the process of cleavage of the Gag polyproteins, by the viral protease, into 4 structural proteins (p17, p24, p7 and p6) and the assembly of those proteins to the matrix (p17), capsid (TCD4+ p24) and nucleocapsid (p7). Following the maturation phase, the virions, which, prior to cleavage, were not mature, are infectious, that is to say ready to infect new cells.

The prevention or inhibition of viral replication can be either partial or total.

According to a particular embodiment, the compound(s) of structure I or a composition or combination comprising it(them) has(have) the ability to prevent, reduce and/or inhibit viral replication in vitro.

According to a particular embodiment, the compound(s) of structure I is(are) the compound Q-VD-OPH or a derivative of the compound Q-VD-OPH (for example a compound of structure I in which part B consists of the amino acid chain VD), said derivative having retained the ability of the compound Q-VD-OPH to prevent, reduce and/or inhibit viral replication in vitro.

Advantageously, the effect tested in vitro is also obtained in vivo, under appropriate use conditions.

The ability of the compound of structure I according to the invention or of a composition or combination comprising said compound of structure I to prevent or inhibit viral replication can be evaluated, for example, in vitro, by flow cytometry, after intracellular labelling of a viral antigen such as p24, as described in the examples below.

According to a particular embodiment, the compound of structure I according to the invention or a composition or combination comprising said compound of structure I is used to prevent, reduce and/or inhibit the synthesis of viral proteins in an animal or human infected by a virus as described in the present application.

The expression "viral proteins" refers to at least one protein of the virus, in particular to at least one structural protein of the virus. The viral proteins whose synthesis can be prevented, slowed, reduced and/or inhibited under the effect of the active ingredients according to the invention, in particular under the effect of the compound(s) of structure I according to the invention, include in particular the envelope, capsid, nucleocapsid proteins, etc., especially for the lentiviruses, the proteins Gag, Pol and Env.

The prevention or inhibition of the synthesis of viral proteins can be partial, or total, or partial for some of the viral proteins and total for the remainder of the viral proteins. When it is partial for all the viral proteins or for some viral proteins, the expression "prevent or inhibit the synthesis of viral proteins" means that, under the effect of one or more active substance(s) according to the invention, in particular under the effect of one or more compound(s) of structure I according to the invention, one or more viral proteins are synthesized in a smaller quantity in the host cell, and are therefore present in a smaller quantity in the host cell or in the cell supernatant, as compared with the synthesis of the same viral proteins in the absence of said active substance(s). When the prevention or inhibition of the synthesis of viral proteins is total, the viral protein(s) is(are) not synthesized in a detectable manner.

Figure 6:
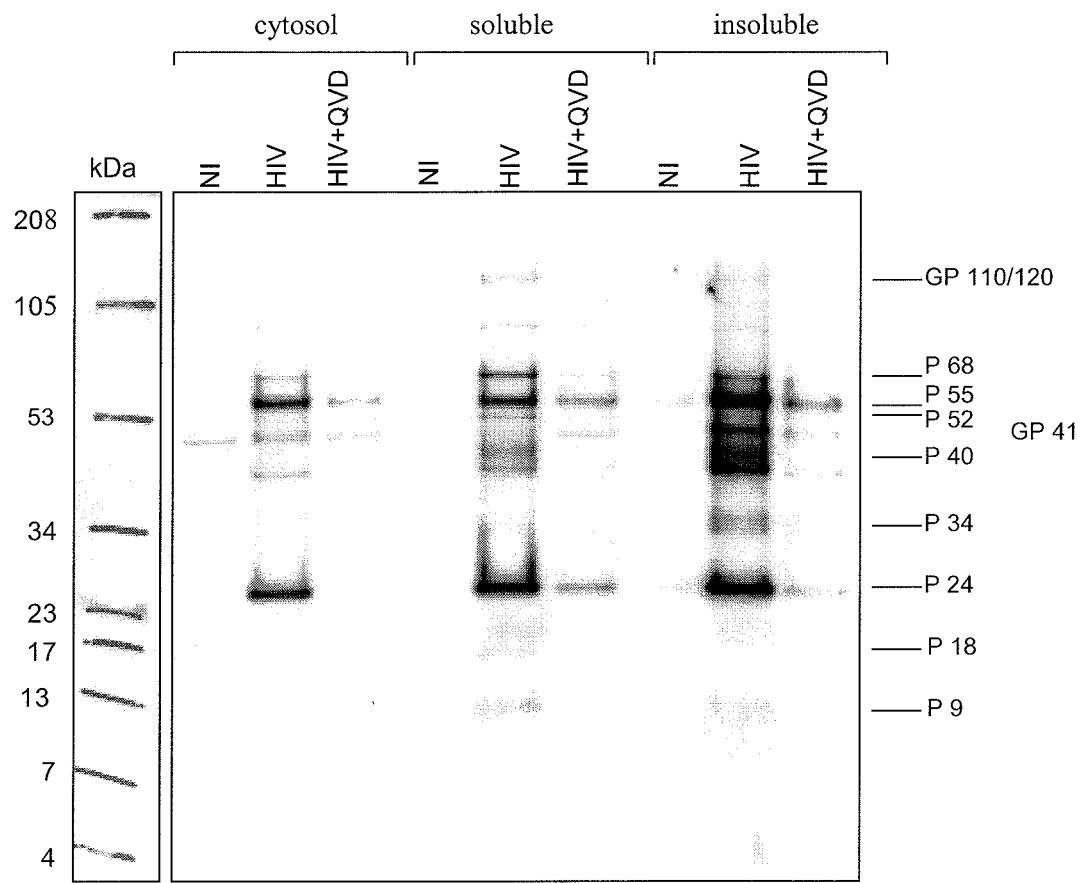

The prevention or inhibition of protein synthesis can be evaluated, for example, by immunotransfer (Western blot), using specific antibodies directed against said viral proteins, as described in Example B6 and FIG. 6.

The compound of structure I according to the invention or a composition or combination comprising said compound can further be used for preventing and/or inhibiting both (i) viral replication, in particular viral protein synthesis, and (ii) the increase in cell death, in particular the increase in the death of the T lymphocytes and more particularly of the CD4+ T cells, induced by a virus as described in the present application, in an animal or human infected by said virus.

The compound(s) of structure I according to the invention or a composition or combination comprising said compound(s) can be used in particular in the treatment or prophylaxis of a viral infection associated with an increase in cell death, in particular an increase in the death of the cells of the immune system and/or of the neuronal cells and/or of the epithelial cells, in an animal or human infected by said virus. The invention is directed more particularly towards viral infections correlated with an increase in the cell death of the T cells, and in particular the CD4+ T cells, in an animal or human infected by a virus, in particular infections by the HIV viruses.

An "increase in cell death" or an "increase in apoptosis" within the scope of the present application means that the percentage cell death is greater than the percentage normally observed in the cell model in question. By way of example, in the case of normal (uninfected) CEM cells, there will be considered to be an increase in cell death when the percentage cell death is greater than 1.7% (background noise observed according to Gandhi et al., 1998). Also by way of example, in a primary culture of healthy activated CD4+ lymphocytes, there will be considered to be an increase in cell death when the percentage cell death is greater than 8% (background noise normally observed). According to a particular embodiment, cell death or apoptosis increases by at least 10%, at least 20% or at least 40%, or even more. This increase can be demonstrated in vitro by any laboratory technique conventionally used to quantify the percentage cell death or apoptosis; for example, in the case of cell death, a simple direct cell count using a microscope will be sufficient. In the case of apoptosis, it is possible to use, for example, the TUNEL (for "terminal deoxyribonucleotidyl transferase (TDT)-mediated dUTP-digoxigenin nick end labelling") technique or to label the cells with acridine orange or measure mitochondrial depolarization.

The expression "a viral infection associated with an increase in cell death" and in particular "a viral infection associated with an increase in apoptosis" is understood as meaning an infection which is generally accompanied, in the more or less long term, by an increase in cell death and in particular in apoptosis. The increase can be the direct and/or indirect result of contamination by a virus as described in the present application.

Prevention or inhibition of the increase in cell death or apoptosis can be partial or total. When it is partial, the expression "prevent and/or inhibit the increase in cell death" or "prevent and/or inhibit the increase in apoptosis" means that, under the effect of one or more active substance(s) according to the invention, in particular under the effect of one or more caspase inhibitor(s) according to the invention, the number of dead cells or the number of apoptotic cells in the host organism or in certain tissues or for certain particular cell types of the host organism is reduced relative to the number observed in the absence of said active substance(s). Cell death is reduced preferably by at least 10%, more preferably at least 30% and yet more preferably at least 50%.

According to a particular embodiment, the compound of structure I according to the invention can be prepared in the form of a pharmaceutical composition further comprising one or more carrier(s), diluent(s) and/or adjuvant(s) or a combination thereof, as well as other active substances. In the case of an injectable administration, there can be chosen especially a formulation in an aqueous, non-aqueous or isotonic solution.

In the present application, the term "carrier" denotes any substrate (that is to say anything which is able to transport at least one active ingredient) which does not interfere with the efficacy of the biological activity of the active substances (in particular the compound(s) of structure I). A large number of carriers are known in the prior art. The carriers used can be, for example, water, a saline solution, serum albumin, a Ringer solution, polyethylene glycol, water-miscible solvents, sugars, binders, excipients, pigments, vegetable or mineral oils, water-soluble polymers, surface-active agents, thickening or gelling agents, cosmetic agents, solubilizing agents, stabilizing agents, preservatives, alkalinizing or acidifying agents or a combination thereof. The formulation of such carriers in the form of a pharmaceutical composition is described especially in "Remington's Pharmaceutical Sciences", 18th edition, Mack Publishing Company, Easton, Pa.

In the present application, the term "diluent" means a diluting agent and includes soluble diluents and insoluble diluents. There is generally used an insoluble diluent when the active ingredient is soluble and a soluble diluent when the active ingredient is insoluble. An "insoluble" active ingredient can be completely insoluble in an aqueous medium or can have limited solubility (that is to say a solubility of less than 10 mg/ml in 250 ml of water at a pH of from 1.0 to 7.5) in an aqueous medium. Examples of insoluble diluents include microcrystalline cellulose, silicified microcrystalline cellulose, hydroxymethylcellulose, dicalcium phosphate, calcium carbonate, calcium sulfate, magnesium carbonate, tricalcium phosphate, etc. Examples of soluble diluents include mannitol, glucose, sorbitol, maltose, dextrates, dextrins, dextrose, etc.

The adjuvants which can be used within the scope of the invention are in particular nucleic acids, peptidoglycans, carbohydrates, peptides, cytokines, hormones or other small molecules. Said adjuvants that are used can be, for example, adjuvants of the non-methylated CpG dinucleotide (CpG) family, adjuvants of the poly IC family and adjuvants of the monophosphoryl lipid A (MPL) family or an analogue thereof.

According to a preferred embodiment, the carrier(s) or diluent(s) or combinations thereof used in the invention are pharmaceutically acceptable substances or a combination of pharmaceutically acceptable substances. A substance or a combination of substances is said to be "pharmaceutically acceptable" when it is suitable for administration to a living being (for example a human or animal) for therapeutic or prophylactic purposes. It is therefore preferably non-toxic for the host to which it is administered.

The terms "administration" and "administer" as used in the present application include any administration, whatever the chosen route of administration.

The routes of administration and the dosages vary according to a variety of parameters, for example according to the condition of the patient, the type of infection and the severity of the infection to be treated, or according to the compound(s) of structure I and the other antiviral agents used.

The compound of structure I according to the invention, the composition according to the invention (in particular the antiviral composition according to the invention) and the constituents of the combination according to the invention can especially be administered to an animal or human in dry form, in solid form (in particular tablet, powder, gelatin capsule, pill, granules, suppository, polymer capsule or compressed tablet, and more precisely accelerated release tablet, enteric-coated tablet or sustained release tablet), in gel form or in the form of a solution or liquid suspension (in particular syrup, injectable, infusible or drinkable solution, microvesicles, liposomes). The compounds can also be in the form of doses in dry form (powder, lyophilisate, etc.) for reconstitution at the time of use using a suitable diluent.

According to their galenical form, the composition according to the invention (in particular the antiviral composition of the invention) and the constituents of the combination of the invention can be administered by the enteral, parenteral (intravenous, intramuscular or subcutaneous), transcutaneous (or transdermal or percutaneous), cutaneous, oral, mucosal, in particular transmucous-buccal, nasal, ophthalmic, otological (in the ear), oesophageal, vaginal or rectal route, or alternatively by the intragastric, intracardiac, intraperitoneal, intrapulmonary or intratracheal routes.

In addition, the compound of structure I, the composition of the invention or the constituents of the combination of the invention can be packaged for administration in the form of a single dose (monodose) or a multiple dose (multidose). In order to increase the effects of the treatment, it is possible to carry out administration in the form of a plurality of successive administrations, repeated on one or more occasions, after a particular time interval. For example, a plurality of administrations can be carried out per day or per week.

The amount of active ingredient administered to an animal or human is a therapeutically effective amount. A "therapeutically effective amount" is an amount sufficient to obtain a significant effect and in particular to bring a significant benefit to a human or animal within the scope of an administration for prophylaxis or treatment as defined in the present application. A therapeutically effective amount is also an amount for which the beneficial effects outweigh any toxic or harmful effect of the active ingredient(s). Such an amount can correspond to an amount sufficient to significantly inhibit viral replication or to bring about the disappearance, reduction or improvement of any existing infection caused by a virus. The therapeutically effective amount varies according to factors such as the state of infection and the age, sex or weight of the animal or human individual. The dosage regimens can be adjusted in order to obtain an optimum therapeutic effect. For example, it is possible to administer from 15 to 50 mg/kg body weight of compound of structure I according to the invention. More specifically, in the case of a human weighing about 60 kg, a therapeutically effective amount of compound of structure I according to the invention can be from 100 to 300 mg/day, administered in from 1 to 3 doses.

The present invention relates also to the use of one or more compound(s) of structure I, in particular the use of the compound Q-VD-OPh, in association with other antiviral agents, in particular other antiretroviral agents, in the prophylaxis and/or treatment of a viral infection. As examples of antiviral agents there may be mentioned, in connection with infection due to HIV, the combined antiretroviral drugs within the scope of highly active antiretroviral therapy (or "HAART").

Accordingly, a particular pharmaceutical composition according to the invention further comprises at least one other antiviral agent.

The present invention therefore relates also to a novel antiviral composition comprising, consisting essentially of or consisting of:
(i) at least one compound of structure I as defined in the present application,
(ii) at least one other antiviral agent.

The compound of structure I can therefore be used in association with an antiviral agent or a plurality of antiviral agents, in particular at least two other antiviral agents. Said other antiviral agent or agents can in particular be antiretroviral agents.

The expression "consists essentially of" as used in the present application means that other minor ingredients or molecules can be present with the active ingredients expressly listed, without affecting the activity of said active ingredients.

The antiviral and antiretroviral agents which can be used within the scope of the present application include in particular:
transcriptase inhibitors, in particular reverse transcriptase inhibitors, for the retroviruses, which are intended to act at the very start of the viral replication cycle, especially reverse transcriptase inhibitors which are intended to act before the viral DNA becomes integrated into the DNA of the host cell and which prevent or inhibit the synthesis of proviral DNA from the viral RNA;
viral protease inhibitors (or antiproteases), which generally act at the end of the viral cycle, during maturation of the newly synthesized viral proteins;
inhibitors of the fusion of the viral envelope with the cell membrane, which are intended to block the penetration of the virus into the cell;
inhibitors of receptors or coreceptors, such as CD4 or BOB;
antisense oligonucleotides;
integrase inhibitors; and
molecules that target other steps of viral multiplication (addressing, integration port).

According to a particular embodiment, said other antiviral agent or agents consist(s) of at least one transcriptase inhibitor and/or at least one viral protease inhibitor.

According to a particular embodiment, the antiviral composition according to the invention comprises, consists essentially of or consists of:
(i) at least one compound of structure I according to the invention,
(ii) at least one transcriptase inhibitor, and
(iii) at least one viral protease inhibitor.

The term "transcriptase inhibitor" as used in the present application includes in particular the nucleoside analogues, the non-nucleoside analogues and the nucleotide analogues of reverse transcriptase.

According to a particular embodiment, the transcriptase inhibitor is a reverse transcriptase inhibitor, in particular an HIV virus reverse transcriptase inhibitor, and more particularly a reverse transcriptase inhibitor selected from the group constituted by:
the nucleoside reverse transcriptase inhibitors of HIV, in particular zidovudine or azidothymidine (AZT), didanosine or ddI, zalcitabine or ddC, stavudine or d4T, lamivudine or 3TC, abacavir or ABC, and emtricitabine or FTC;
the non-nucleoside reverse transcriptase inhibitors of HIV, in particular nevirapine, efavirenz and delavirdine; and the nucleotide analogues of the reverse transcriptase of HIV, in particular tenofovir or bis-POC-PMPA.

According to a particular embodiment, one of the transcriptase inhibitors used is AZT.

The term "protease inhibitor" as used in the present application includes in particular peptidomimetic molecules and molecules of the non-peptide type. "Peptidomimetic molecules" are peptides which mimic the natural enzyme substrate and fix to the protease substrate binding sites, preventing cleavage of the protein precursors (for example Gag and Gag-Pol for HIV or SIV), which leads to the production of defective and non-infectious viral particles.

According to a particular embodiment, the viral protease inhibitor is a protease inhibitor of an HIV virus and in particular a viral protease inhibitor selected from the group constituted by the following peptidomimetic molecules: Indinavir or IDV, Nelfinavir or NLFN, Saquinavir or SQN, Ritonavir or RTN, Amprenavir, Lopinavir. According to a particular embodiment, one of the HIV viral protease inhibitors used is Indinavir.

According to a particular embodiment, at least one of the other antiviral agents according to the invention is a fusion inhibitor, in particular an HIV virus fusion inhibitor, for example enfuvirtide. A "fusion inhibitor" is understood as being an inhibitor which acts in the first stage of replication of the virus by preventing fusion between the viral envelope and the cell membrane, for example by competitive inhibition.

According to a particular embodiment, said antiviral composition can further comprise one or more carrier(s), diluent(s) and/or adjuvant(s) or a combination thereof as defined in the present application.

According to a particular embodiment, at least two compounds of the antiviral composition or of the combination according to the invention act in "synergy". This means that it is possible by means of said antiviral composition or said combination to obtain a prophylactic or therapeutic effect that is superior to the sum of the individual effects of each of the compounds acting in synergy.

According to a particular embodiment, the compound(s) of structure I and at least one of the other antiviral agents act in synergy and, in particular, the compound(s) of structure I act(s) in synergy with at least one of the other antiviral agents. The results presented in the present invention show that a compound such as Q-VD-OPh is capable of acting in synergy with other antiviral agents, and in particular with AZT and with Indinavir, to inhibit viral replication and to inhibit the death of the CD4+ T lymphocytes induced by the viral infection.

The use of a compound of structure I, in particular the use of the compound Q-VD-OPh, or of a composition or combination comprising such a compound can therefore enable a treatment based on one or more other antiviral agents, in particular an antiviral treatment that is not very effective against HIV or SIV viruses, to be improved or potentiated. The term "potentiate" means that the use of one or more compounds of structure I according to the invention makes it possible to obtain a prophylactic or therapeutic effect that is superior to the prophylactic or therapeutic effect obtained using said other antiviral agent(s) alone or in combination with other medicament regimes.

In so far as the compounds of structure I are able to potentiate the effect of other antiviral agents, and even act in synergy with said other antiviral agent(s), the use of one or more compounds of structure I can also allow the doses of other antiviral agents that are used to be reduced without reducing the efficacy of the treatment, and even while increasing the efficacy of the treatment.

Another aspect of the present invention relates, therefore, to the use of one or more compound(s) of structure I, in particular the use of the compound Q-VD-OPh, in the production of a medicament for potentiating, for increasing a prophylactic or therapeutic effect of one or more other antiviral agents as defined in the present application and/or for reducing the amount of the other antiviral agents administered to a human or animal.

The present invention relates also to a compound of structure I, in particular the compound Q-VD-OPh, for use in potentiating, in increasing a prophylactic or therapeutic effect of one or more other antiviral agents as defined in the present application and/or in reducing the amount of the other antiviral agents administered to a human or animal.

According to another aspect of the present invention, the active ingredients are combined in a combination (or kit) for use in an antiviral therapy.

Accordingly, the present invention relates also to a combination (or kit) comprising, consisting essentially of or consisting of:
(i) at least one compound of structure I and
(ii) at least one other antiviral agent, in particular at least one other antiretroviral agent, in which compounds (i) and (ii) are separate from one another. Compounds (i) and (ii) of said combination are as defined in the present application. They can be administered to the human or animal body simultaneously and/or sequentially, separately in terms of time. It is in fact possible that some constituents of said combination do not necessarily exert their common activity simultaneously or immediately.

The expression "combination" (or kit) refers to the association, in the posology of a treatment intended for a human or animal infected by a virus, of at least two compounds suitable for use in an antiviral treatment in an animal or human:
(i) at least one compound of structure I and
(ii) at least one other antiviral agent as defined in the present application.

Constituents (i) and (ii) form a functional unit by virtue of a common indication, which is the implementation of an antiviral treatment.

The combination can also comprise a plurality of compounds of structure I, for example 2, 3 or 4 or more, and/or a plurality of other antiviral agents, in particular 2, 3, 4 or more.

Such a combined therapy is intended most particularly for the prophylaxis and/or treatment of viral infections in a human or animal infected by a virus as defined in the present application.

The term "simultaneously" and the expression "simultaneous administration" mean that compounds (i) and (ii) of said combination are administered at the same time, at the same moment, to a human or animal.

According to a particular embodiment, compounds (i) and (ii) of said combination are present in two distinct compositions. "Present in two distinct compositions" is understood as meaning that said compounds are physically separate. They are then employed, administered separately, without prior mixing, in several (at least two) dosage forms (for example two distinct capsules). Said combination therefore corresponds to a presentation of the compound(s) (i) on the one hand and of the compound(s) (ii) on the other hand, in distinct compositions. Because compound(s) (i) is(are) not mixed with compound(s) (ii), the different compounds (i) and (ii) are not chemically modified and can consequently be administered as described in the notice(s) of compliance (AMM) covering the compound(s).

In the case where compounds (i) and compounds (ii) are administered sequentially in terms of time, the sequence of administration is not important, it being possible for administration of compound(s) (i) to precede or follow administration of compound(s) (ii). According to a particular embodiment, compound (i) or at least one of compounds (i) is administered before compound (ii) or at least one of compounds (ii) is administered. Alternatively, compound (ii) or at least one of compounds (ii) can be administered before compound (i) or at least one of compounds (i) is administered.

The expression "sequential administration" means that said or one of said compounds (i) and said or one of said compounds (ii) of the combination or kit according to the invention are administered not simultaneously but separately in terms of time, one after the other.

The term "precede" or "preceding" is used when a compound (or a plurality of compounds) of the combination or kit according to the invention is administered a few minutes or several hours, or even several days, prior to administration of the other compound(s) of said combination or kit. Conversely, the term "follow" or "following" is used when a compound (or a plurality of compounds) of the combination or kit according to the invention is administered a few minutes or several hours, or even several days, after administration of the other compound(s) of said combination or kit.

Furthermore, according to a particular embodiment, compounds (i) and (ii) of the combination or kit according to the invention are formulated for administration at an interval of one or several hours, preferably a 1-, 2-, 3- or 4-hour interval, more preferably a 1- or 2-hour interval, yet more preferably a 1-hour interval.

The compound(s) (i) and the compound(s) (ii) of the combination can be formulated to facilitate their ingestion and, in particular, can be formulated with one or more carrier(s), diluent(s) or adjuvant(s) as defined above, or a combination thereof.

In addition, the compound(s) (i) and the compound(s) (ii) of the combination or kit according to the invention can be administered by the same route of administration or, on the other hand, by distinct routes of administration. The possible galenical forms and routes of administration are those described above.

According to a particular embodiment, said other antiviral agent(s) consist(s) of at least one transcriptase, especially reverse transcriptase, inhibitor as defined in the present application and/or at least one viral protease inhibitor as defined in the present application.

Preferably, at least two other antiviral agents are used. According to a particular embodiment, therefore, the composition according to the invention comprises:
(i) at least one compound of structure I according to the invention,
(ii) at least one transcriptase inhibitor, and
(iii) at least one viral protease inhibitor.

The present invention relates also to an antiviral composition or a combination according to the invention for use as a medicament, in particular as an antiviral agent and more particularly as an antiretroviral agent. More precisely, said antiviral composition or said combination can be used in the prophylaxis and/or treatment of a viral infection, in particular an infection caused by a virus as defined in the present application, and more particularly for inhibiting viral replication, in a mammal or human.

The present invention relates also to the use of an antiviral composition or of a combination according to the invention in the production of a pharmaceutical composition for the prophylaxis and/or treatment of a viral infection, in particular an infection caused by a virus as defined in the present application, in a mammal or human.

The invention relates also to a method of treating an animal or human infected by a virus as described in the present application, said method comprising at least one step of administration of the compound(s) of structure I according to the invention, of the antiviral composition according to the invention or of the constituents of the combination according to the invention.

Said treatment method is, in particular, suitable for and intended for use in the prophylaxis and/or treatment of a viral infection, in particular in a human or animal infected by a virus as defined in the present application.

More precisely, said treatment method can be used to prevent and/or inhibit viral replication in an animal or human infected by a virus.

Furthermore, said treatment method can be used to prevent and/or inhibit the increase in cell death in an animal or human infected by a virus, in particular the increase in the death of the T lymphocytes and more particularly the increase in the death of the CD4 T lymphocytes.

The treatment method according to the invention is considered to have achieved the expected therapeutic effect if it permits a reduction of at least 10%, preferably 30%, and more preferably at least 50%, in viral replication in the treated animal or human. The therapeutic effect can also be defined in relation to the clinical standards developed for measuring the beneficial effects of medicaments on HIV infection. A drug has a beneficial effect if it halves the plasma viral load in humans. A drug has a super-beneficial effect if it divides the plasma viral load in humans by 100.

BRIEF DESCRIPTION OF THE DRAWING FIGURES

FIG. 1: Immunoblot (Western blot) showing the effectiveness of Q-VD-OPh in inhibiting activation of caspase-3 and -8. $CD4^+$ T lymphocytes were or were not infected by the HIV-1 virus (incubation: 2 hours) and then stimulated by Concanavalin A and IL-2 (incubation: 2 hours). After stimulation, the inhibitor Q-VD-OPh was added to the cell culture at a final concentration of 10 µM and then also added 36 hours after infection (d3) and 96 hours after infection (d4). The immunoblot was carried out on the 6th day post-infection. Caspase-3 and -8 were detected using the anticaspase antibodies indicated above. NI: control cells ($CD4^+$ T cells not infected by HIV-1 and not treated with Q-VD-OPh); HIV: $CD4^+$ T cells infected by HIV-1 but not treated with Q-VD-OPh; HIV+QVD: $CD4^+$ T cells infected by HIV-1 and then cultivated in the presence of 10 µM of Q-VD-OPh. Actin serves as the control for the protein load of the gel. The molecular weight marker RPN 800 (Amersham) was used.

Figure 2:
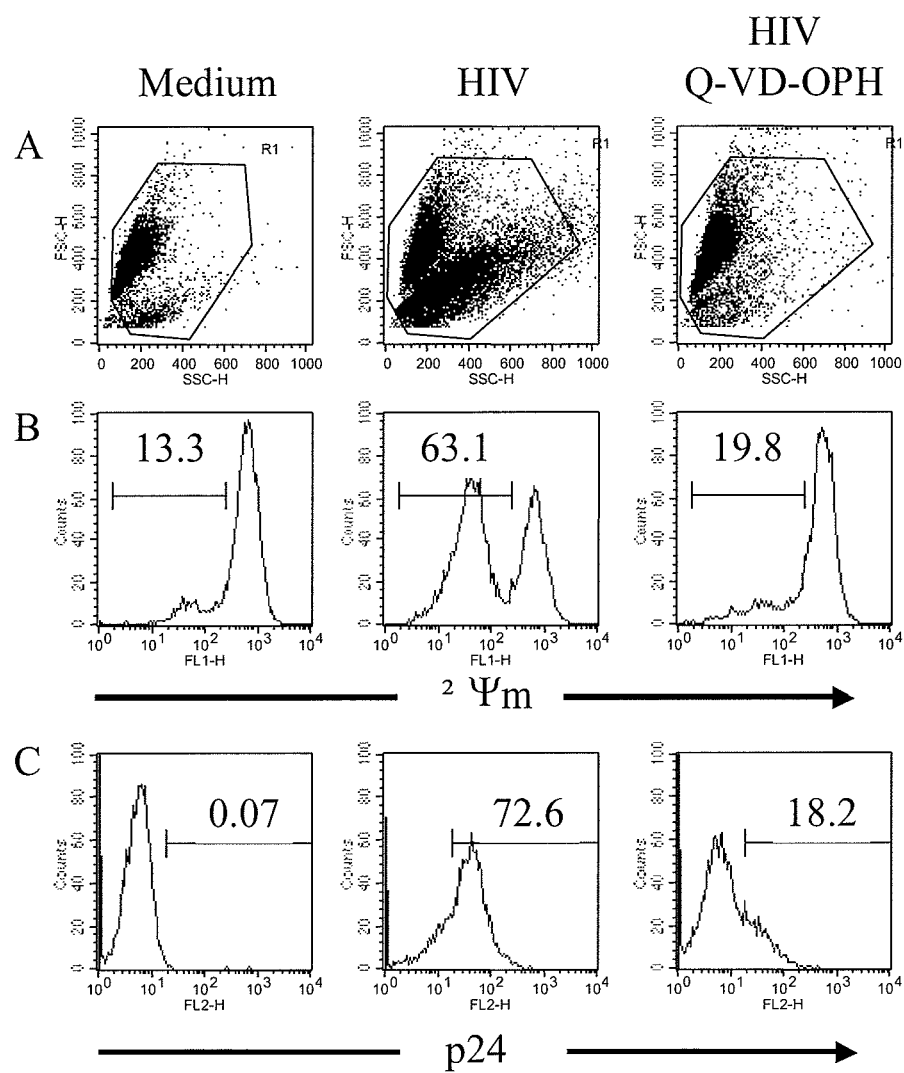

FIG. 2: Analysis of the CD4+ T lymphocytes by flow cytometry on the 5th day after infection by HIV-1 and after stimulation by Concanavalin A and IL-2. A. Analysis of the size and granulometry of the CD4+ T lymphocytes. B. Determination of the percentage of CD4+ cells having a mitochondrial impairment ($\Delta\Psi m$). C. Determination of the percentage of CD4+ cells infected by HIV after intracellular labelling of the p24 viral antigen. NI: uninfected CD4+ T lymphocytes; HIV: CD4+ T lymphocytes infected by HIV-1; HIV Q-VD-OPh: CD4+ T lymphocytes infected by HIV-1 (incubation: 2 hours), activated by ConA and IL2 (incubation 2 hours) and then incubated with Q-VD-OPh (10 µM final); Q-VD-OPh is added 36 hours (day 3) and 96 hours (day 4) after the start of the infection.

Figure 3:
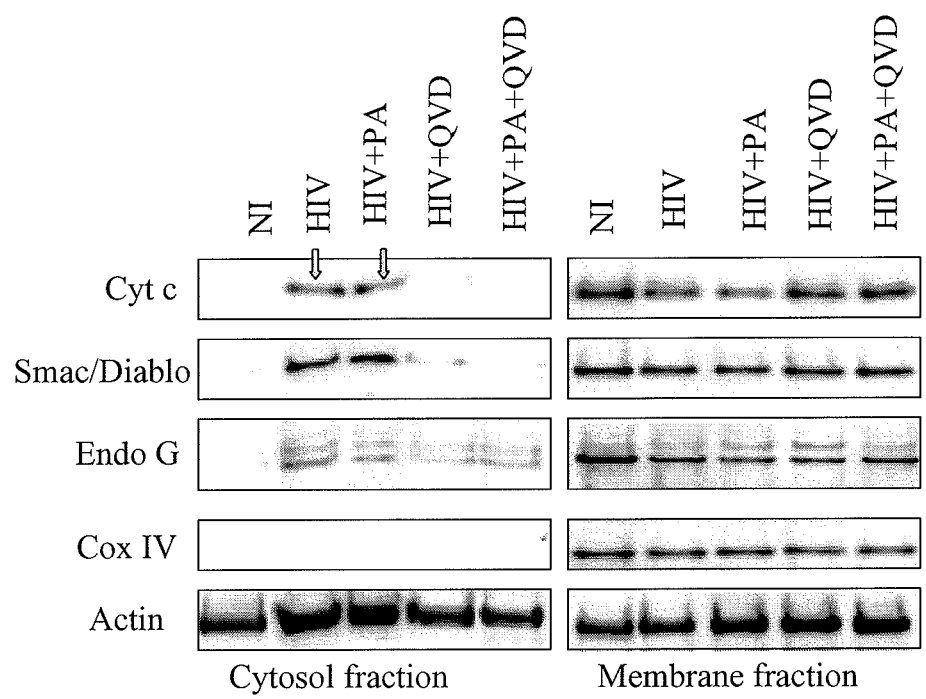

FIG. 3: Immunoblot (Western blot) showing the effect of Q-VD-OPh on mitochondrial damage resulting from viral replication. Primary CD4+ T cells were infected with HIV- Lai and stimulated with a ConA/IL-2 cocktail and then treated or not treated with 10 μM of Q-VD-OPh (QVD) and/or 10 μM of pepstatin A (PA) immediately after stimulation and then 36 hours (day 3) and 96 hours (day 4) after infection. On the 5th day post-infection, the cells were fractionated into two parts: the membrane fraction and the cytosol fraction. The relocalization of the apoptogenic factors Cytochrome c (Cyt c), Smac/Diablo and Endonuclease G (EndoG) was then evaluated by immunotransfer (Western blot). The proteins Cytochrome c, Smac/Diablo and EndoG were detected using the antibodies indicated above. The proteins Cox IV and actin detected by means of the anti-subunit IV antibodies (clone 1068 Molecular Probe) and anti-actin antibodies (SIGMA), respectively, were used as the control for the fractionation procedure and as the control for the protein load of the gel, respectively.

Figure 4:
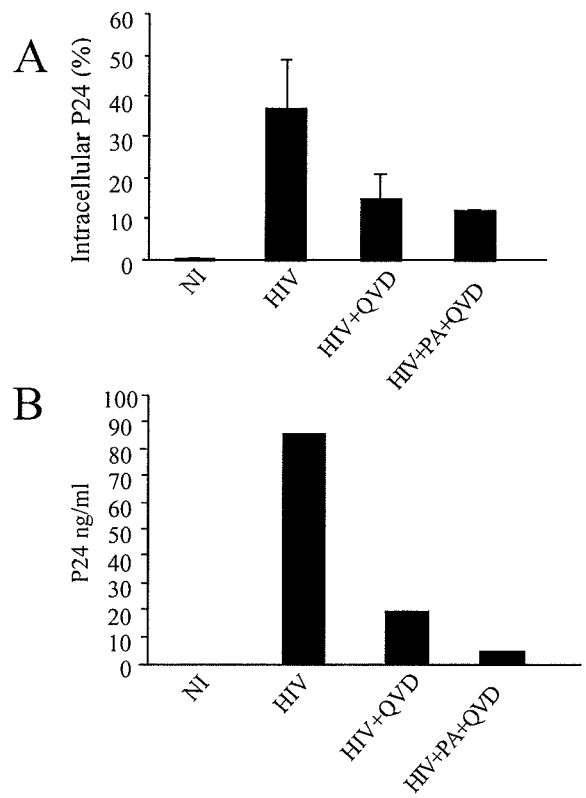

FIG. 4: Graphic representation showing the effect of Q-VD-OPh on replication of the HIV-1 virus. A. Determination of the percentage of CD4+ T lymphocytes infected by HIV-1 by flow cytometry, after intracellular labelling of the p24 viral antigen. B. ELISA assay of the p24 viral antigen in the culture supernatants. All the cells were stimulated by Con A and IL2 within 24 hours of infection. The parameters were measured on the 6th day post-infection. NI: uninfected CD4+ T lymphocytes; HIV: CD4+ T lymphocytes infected by HIV-1; HIV+QVD and HIV+PA+QVD: CD4+ T lymphocytes infected by HIV-1, to which there were administered, on the 3rd day post-infection and then every day, Q-VD-OPh (QVD) or Q-VD-OPh (QVD) and pepstatin A (PA), respectively.

Figure 5:
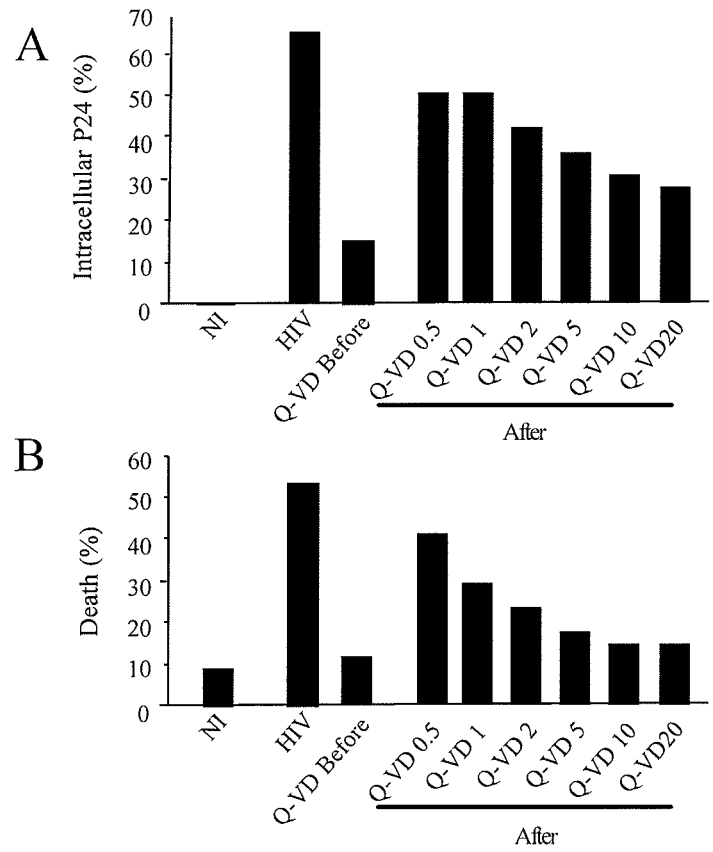

FIG. 5: The time at which Q-VD-OPh is administered to the CD4+ T lymphocytes influences the inhibition of cell death and the inhibition of viral replication. CD4+ T lymphocytes were or were not infected with HIV-Lai and stimulated with a ConA/IL2 cocktail and then treated or not treated with 10 μM of Q-VD-OPh and/or 10 μM of pepstatin A. There were determined, by flow cytometry, the percentage of CD4+ T lymphocytes infected by HIV after intracellular labelling of the p24 antigen (A) and the percentage of dead CD4+ T lymphocytes (B) on the 5th day after infection by HIV-1. The parameters were measured on the 5th day post-infection. NI: CD4+ T lymphocytes not infected by HIV-1; HIV: CD4+ T lymphocytes infected by HIV-1; Q-VD: CD4+ T lymphocytes infected by HIV-1, to which there were administered Q-VD-OPh and pepstatin A (PA); in the first case (Before), Q-VD-OPh and PA were administered between 1 and 2 hours before infection by HIV-1 and stimulation by Concanavalin A and IL-2 and then on d3 and d4 post-infection, at a final concentration of 10 μM. In the second case (After), Q-VD-OPh and PA were administered immediately after infection by HIV-1 and on d3 and d4 post-infection at different final concentrations (0.5; 1; 2; 5; 10 and 20 μM).

FIG. 6: Immunoblot (Western blot) showing the inhibitory effect of Q-VD-OPh on the expression of a group of HIV-1 proteins in primary CD4+ cells. Protein extracts prepared on the 6th day of culturing from uninfected CD4+ T lymphocytes (NI) or CD4+ T lymphocytes infected by the HIV-1 virus and then cultivated in the absence of Q-VD-OPh (HIV) or in the presence of Q-VD-OPh (HIV+Q-VD-OPh) were fractionated into three parts: the cytosol fractions (cytosol), the soluble membrane fractions (soluble) and the insoluble membrane fractions (insoluble). Q-VD-OPh was added at a final concentration of 10 μM, immediately after infection and then 36 hours (d3) and 96 hours (d4) post-infection. The proteins specific to HIV were detected using a mixture of sera from HIV+ patients. They are indicated on the right of the immunoblot. The molecular weight marker RPN 800 (Amersham) was used.

Figure 7:
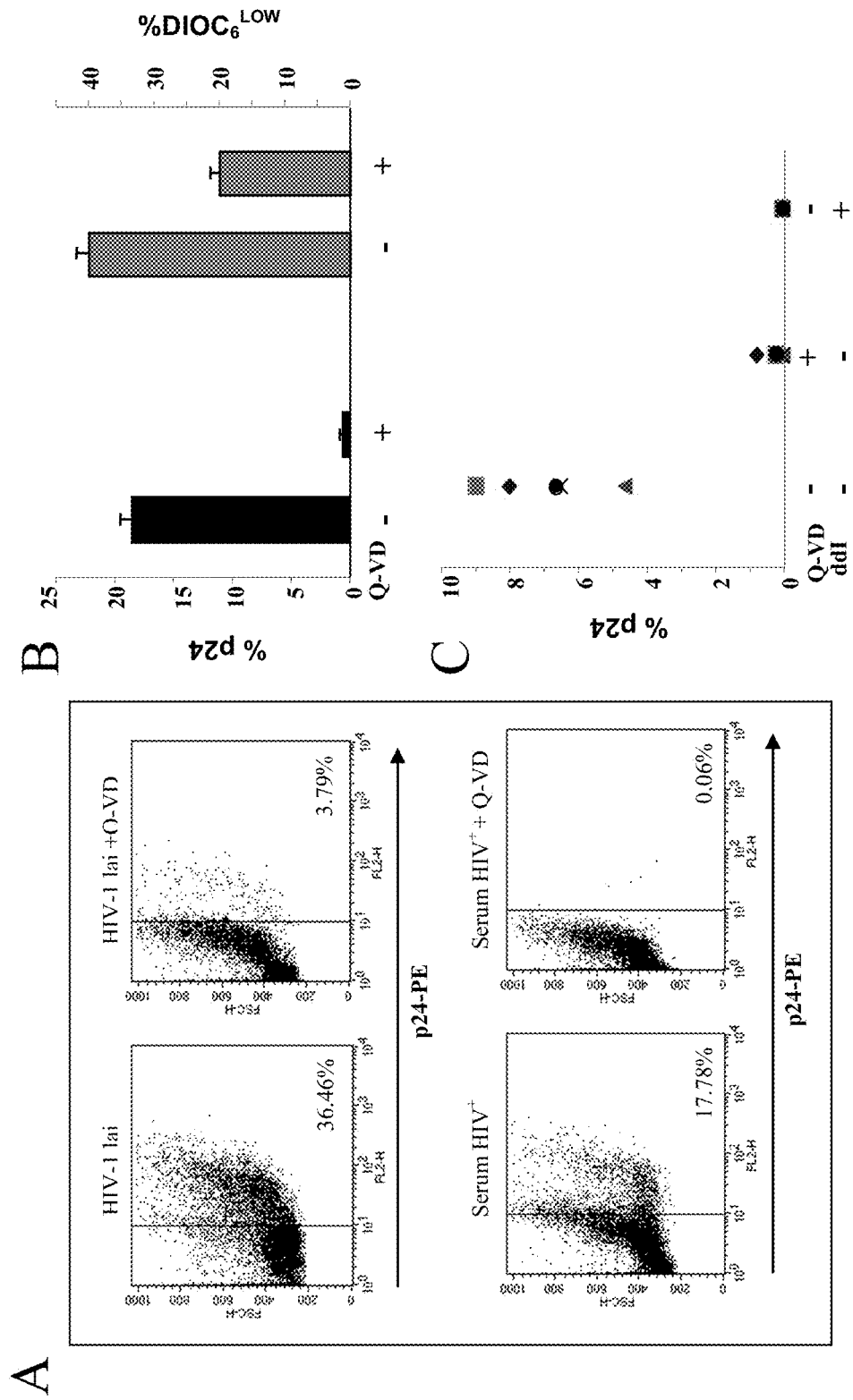

FIG. 7: Graphic representation showing the effect of Q-VD-OPh on primary HIV-1 strains. In all cases (A, B and C), the CD4+ T lymphocytes were stimulated with concanavalin A and IL2 (stimulation being carried out before or during administration of Q-VD-OPh), and Q-VD-OPh was added at a final concentration of 10 μM, immediately after infection and then 36 hours (d3) and 96 hours (d4) post-infection. A. Analysis by flow cytometry of viral replication in CD4+ T lymphocytes infected with the HIV-1Lai virus or with the serum of a chronic HIV+ patient (strain with X4/R5 dual tropism) and then cultivated in the absence or presence (+Q-VD) of Q-VD-OPh. The percentage of CD4+ cells infected by HIV was determined after intracellular labelling of the p24 viral antigen on the 5th day post-infection in the case of the HIV-Lai virus and on the 6th day post-infection in the case of the serum. PE: phycoerythrin, fluorochrome (emission at 578 nm) coupled to the anti-p24 antibody. B. Quantification of viral replication (on the left) and of cell death by measurement of mitochondrial depolarization (on the right) in CD4+ T lymphocytes infected with the serum of the chronic HIV+ patient. C. Analysis of the replication of five viral isolates from HIV+ patients, with R5 tropism, in the absence (−) or in the presence (+) of Q-VD-OPh or of a final concentration of 1 μM of didanosine (ddI, SIGMA), a reverse transcriptase inhibitor also called Vivex EC® (Bristol-Myers Squibb).

Figure 8:
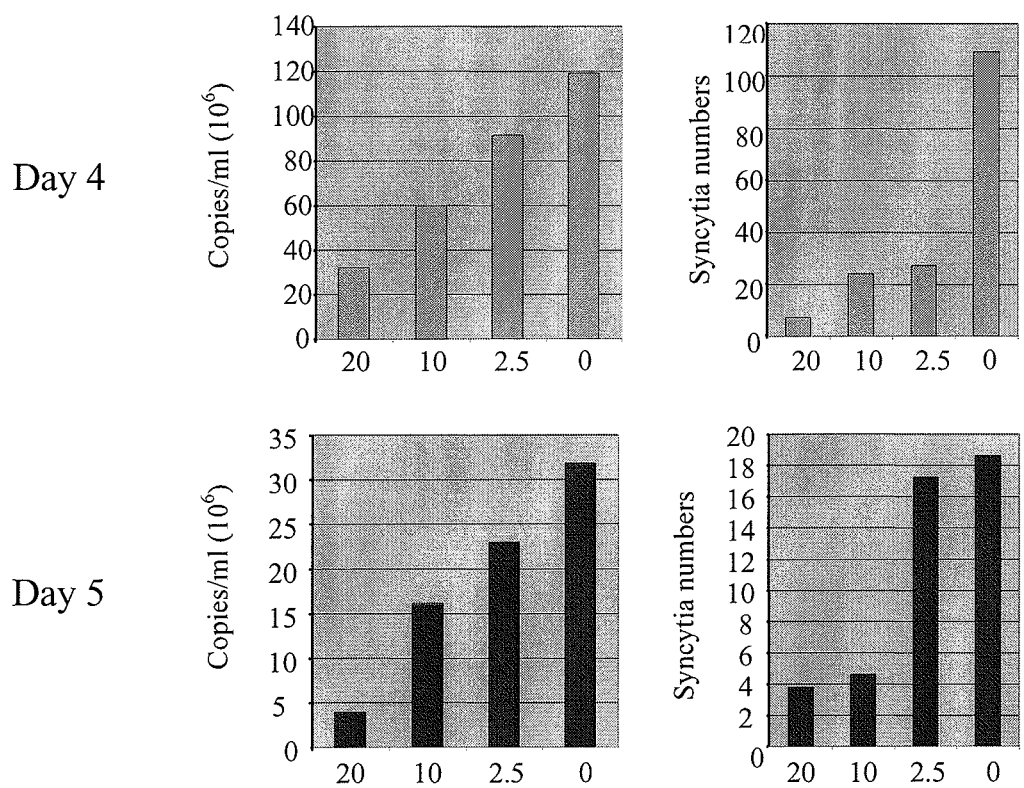

FIG. 8: Graphic representation showing the inhibitory effect of Q-VD-OPh on replication of the SIVmac251 virus and the formation of syncitia. The cell line CEMx174 was infected with 200 AID50 (infectious dose necessary for 50% of the animals to be infected) of the strain SIVmac251. Two hours after infection, the cell line was treated with different concentrations of inhibitor Q-VD-OPh (final concentration of 20, 10 or 2.5 μM) or was not treated (0 μM). On the 4th and 5th days post-infection, viral production in the culture supernatant was evaluated by RT-PCR (Taqman) and the number of syncytia was evaluated using an optical microscope.

Figure 9:
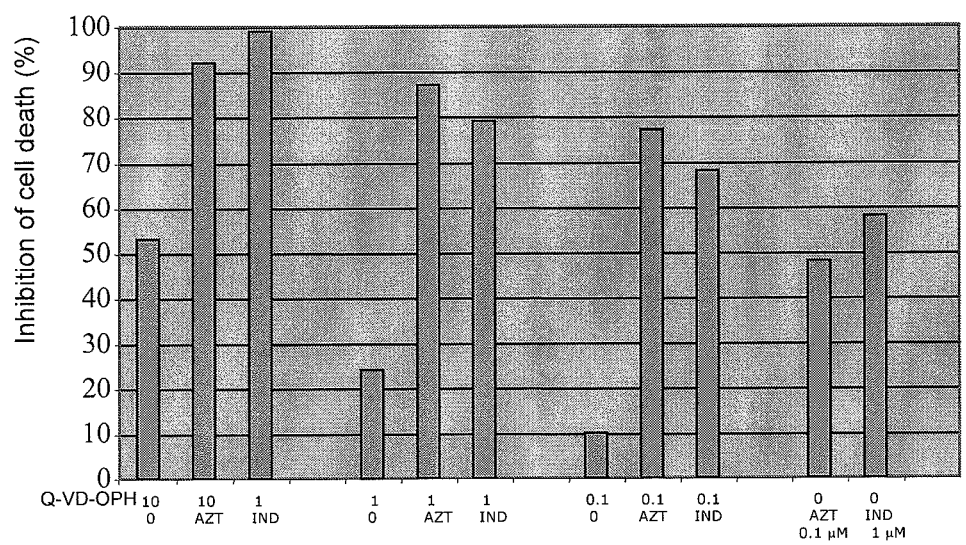

FIG. 9: Graphic representation showing a synergistic effect of Q-VD-OPh with AZT and Indinavir. Primary CD4+ T cells infected by the HIV-Lai virus and then stimulated with concanavalin A and IL-2 were treated 96 hours after infection with different concentrations of Q-VD-OPh (0, 0.1, 1 and 10 μM) in the absence or presence of azidothymidine (AZT; 0.1 μM) or Indinavir (IND; 1 μM). Inhibition of cell death was quantified by flow cytometry on the 5th day post-infection. It is expressed as follows:

(% cell death induced by HIV in the absence of treatment–% cell death induced by HIV in the presence of treatment)/(% cell death induced by HIV in the absence of treatment–% cell death in the control)×100.

Figure 10:
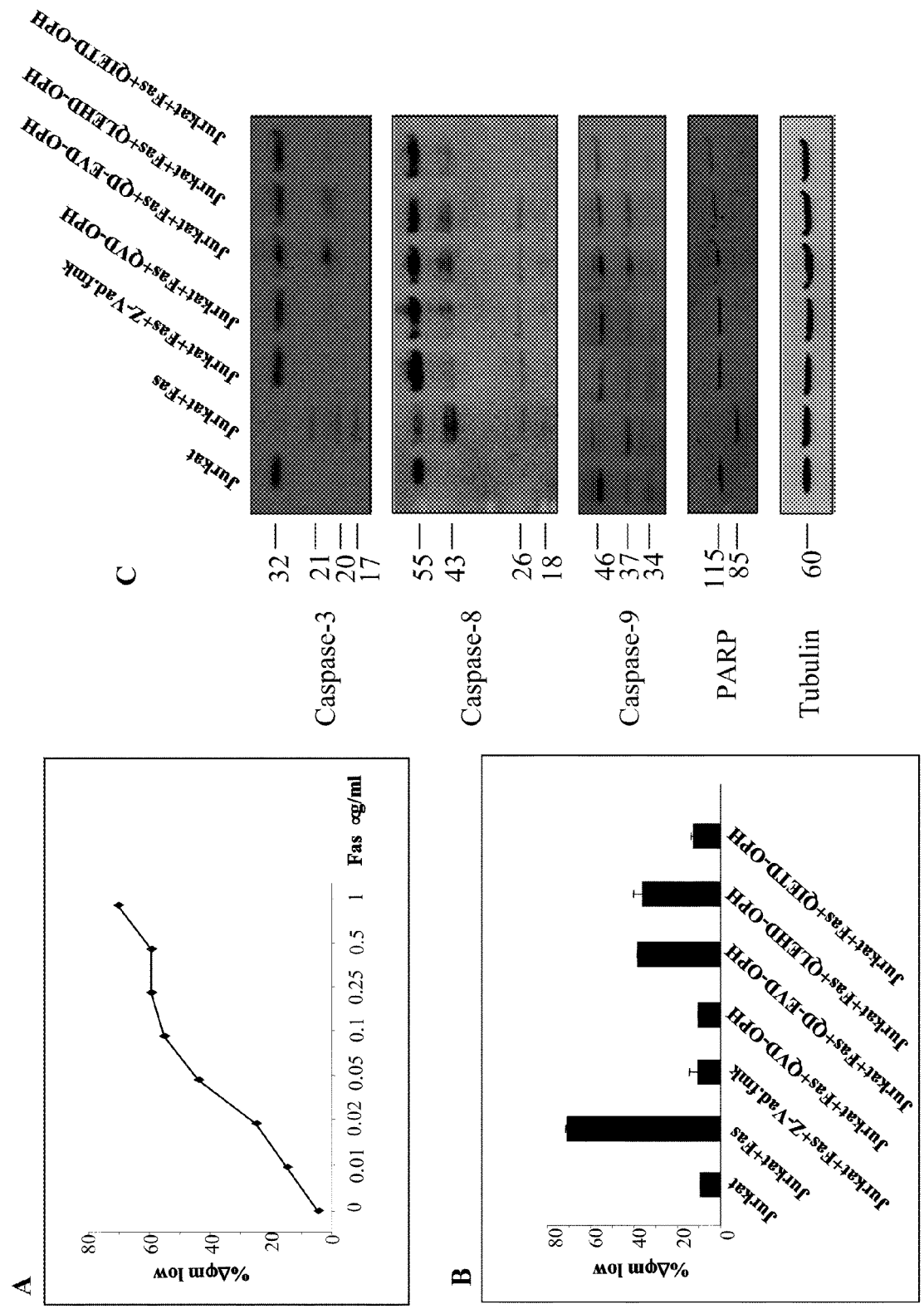

FIG. 10. Analysis by flow cytometry of the fall in the mitochondrial transmembrane potential (% Δϕm low) starting from Jurkat cells incubated in the absence or presence of different concentrations of anti-CD95 (A) and in the absence or presence of 0.25 μg/ml of anti-CD95 and of different caspase inhibitors (B). C. Analysis by immunoblot of Jurkat cell extracts treated in the presence or absence of anti-CD95 and of different caspase inhibitors.

Figure 11:
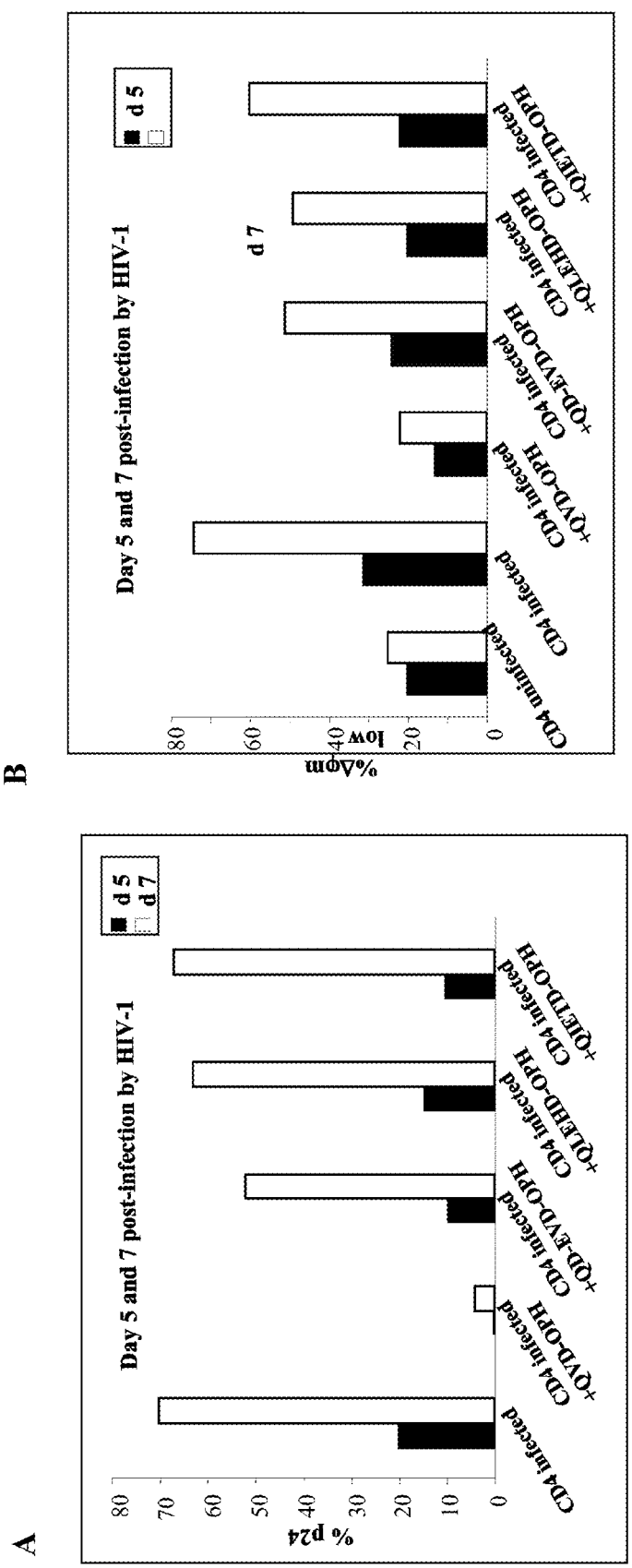

FIG. 11. Analysis by flow cytometry of the internal viral protein p24 (A) and of the fall in the mitochondrial transmembrane potential (% Δϕm low; B) on the 5th (d5) and 7th (d7) day post-infection in primary CD4+ T cells infected by the strain HIV-Lai, after stimulation by Concanavalin A and IL-2 and in the presence or absence of 10 μM of different caspase inhibitors.

Figure 12:
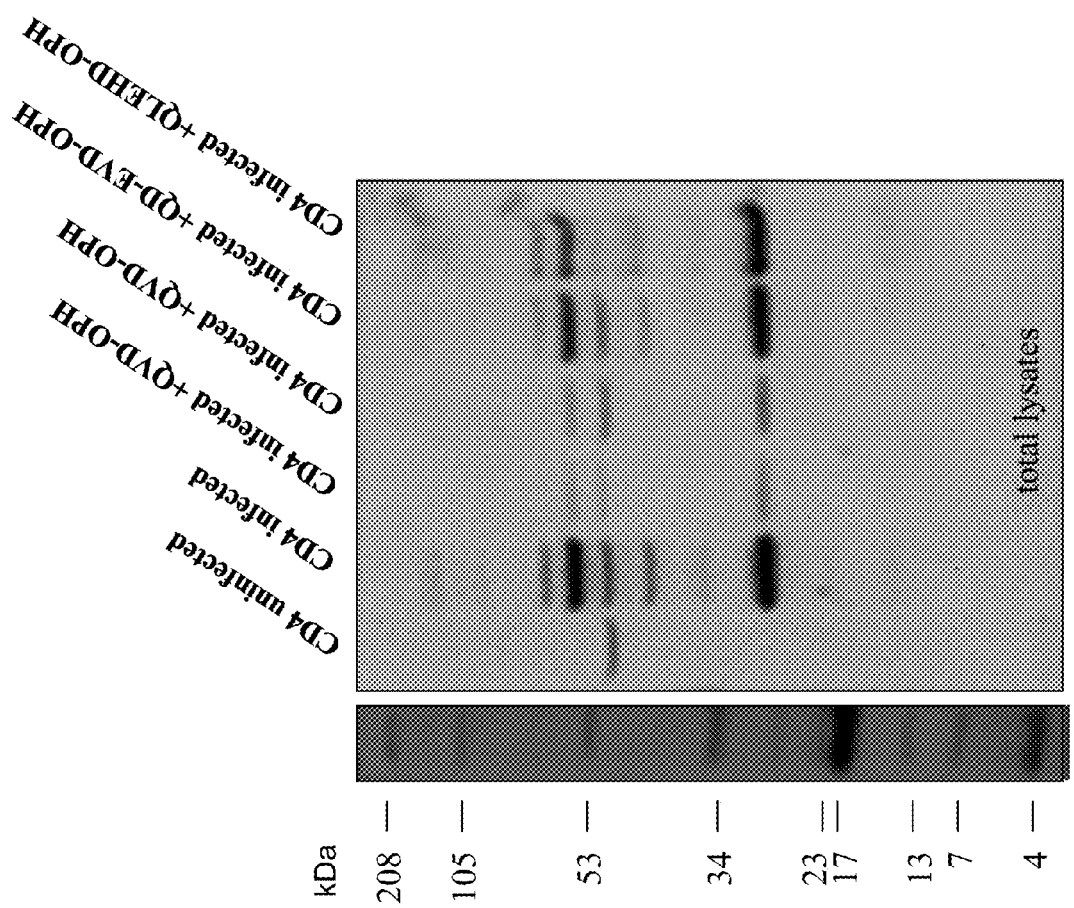

FIG. 12. Analysis by immunoblot of the quantity of HIV viral proteins produced from extracts of primary CD4 T cells infected by the strain HIV-Lai in the presence or absence of different caspase inhibitors.

Figure 13:
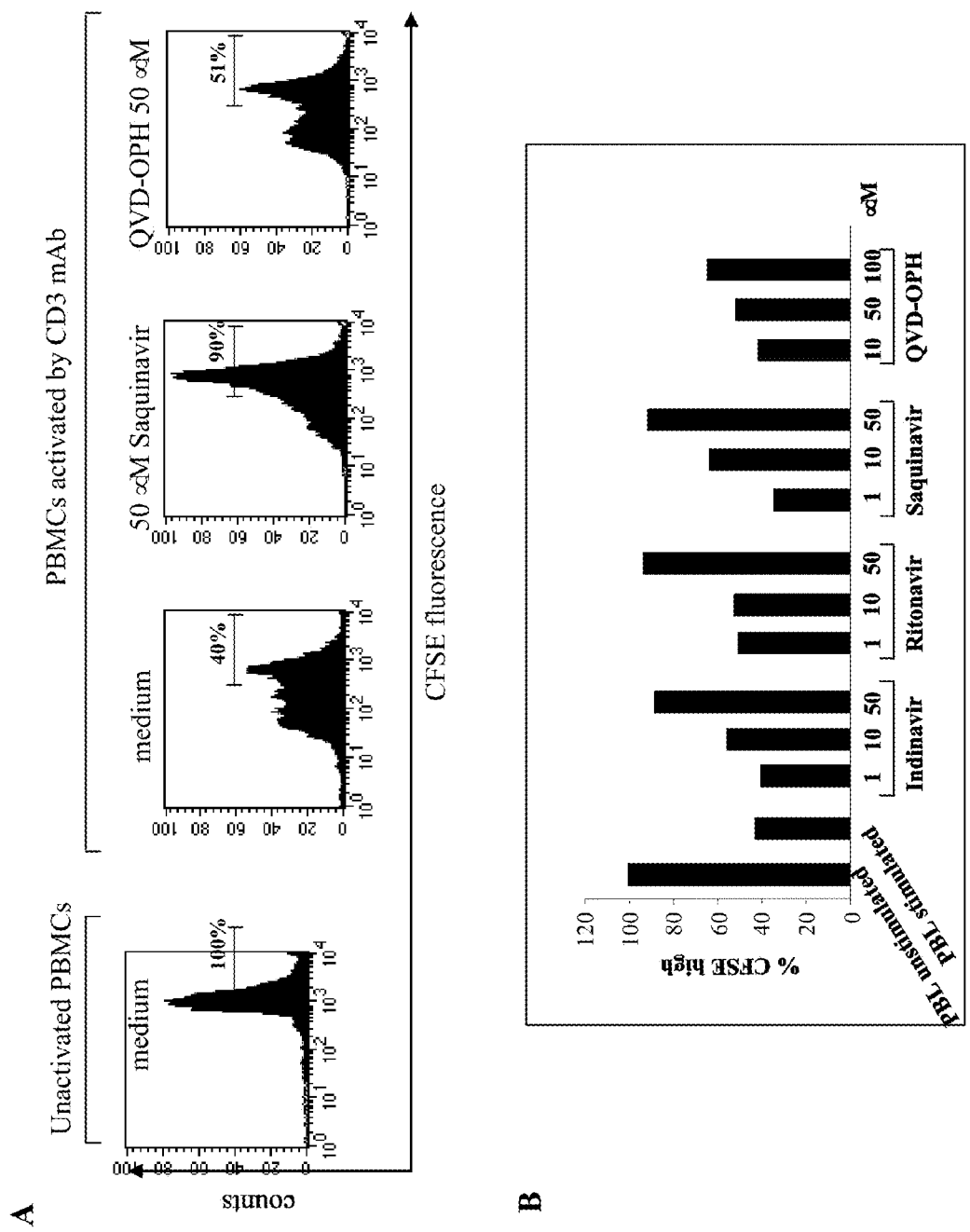

FIG. 13. Analysis by flow cytometry of lymphocyte proliferation after 4 and 5 days' stimulation by 1 μg/ml of anti-CD-3, in the presence or absence of HIV antiproteases or of QVD-OPH.

Figure 14:
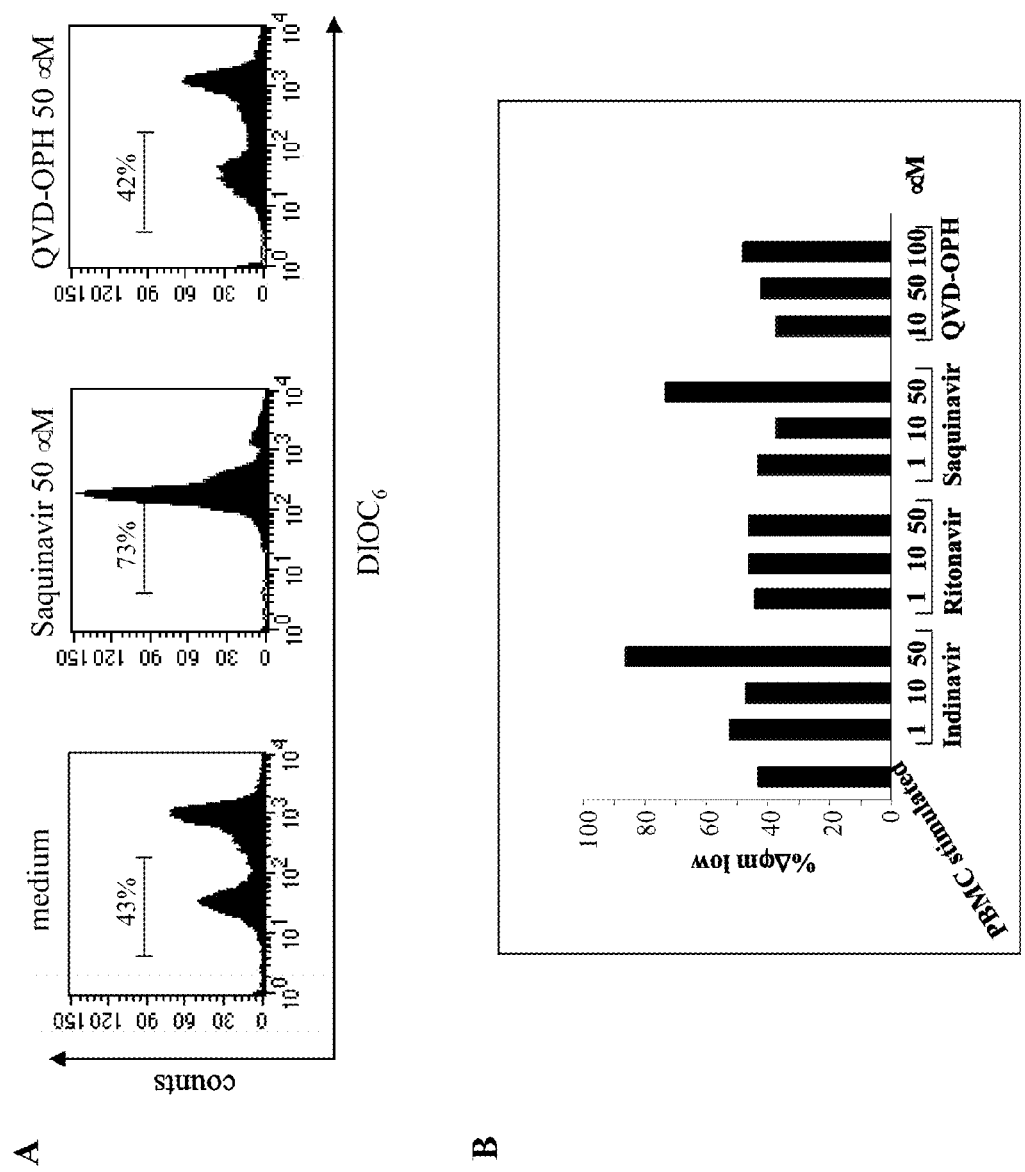

FIG. 14. Analysis of the fall in the mitochondrial transmembrane potential (% Δϕm low) by flow cytometry starting from cells stimulated by 1 μg/ml of anti-CD-3 in the presence or absence of different HIV antiproteases and of QVD-OPH.

Figure 15:
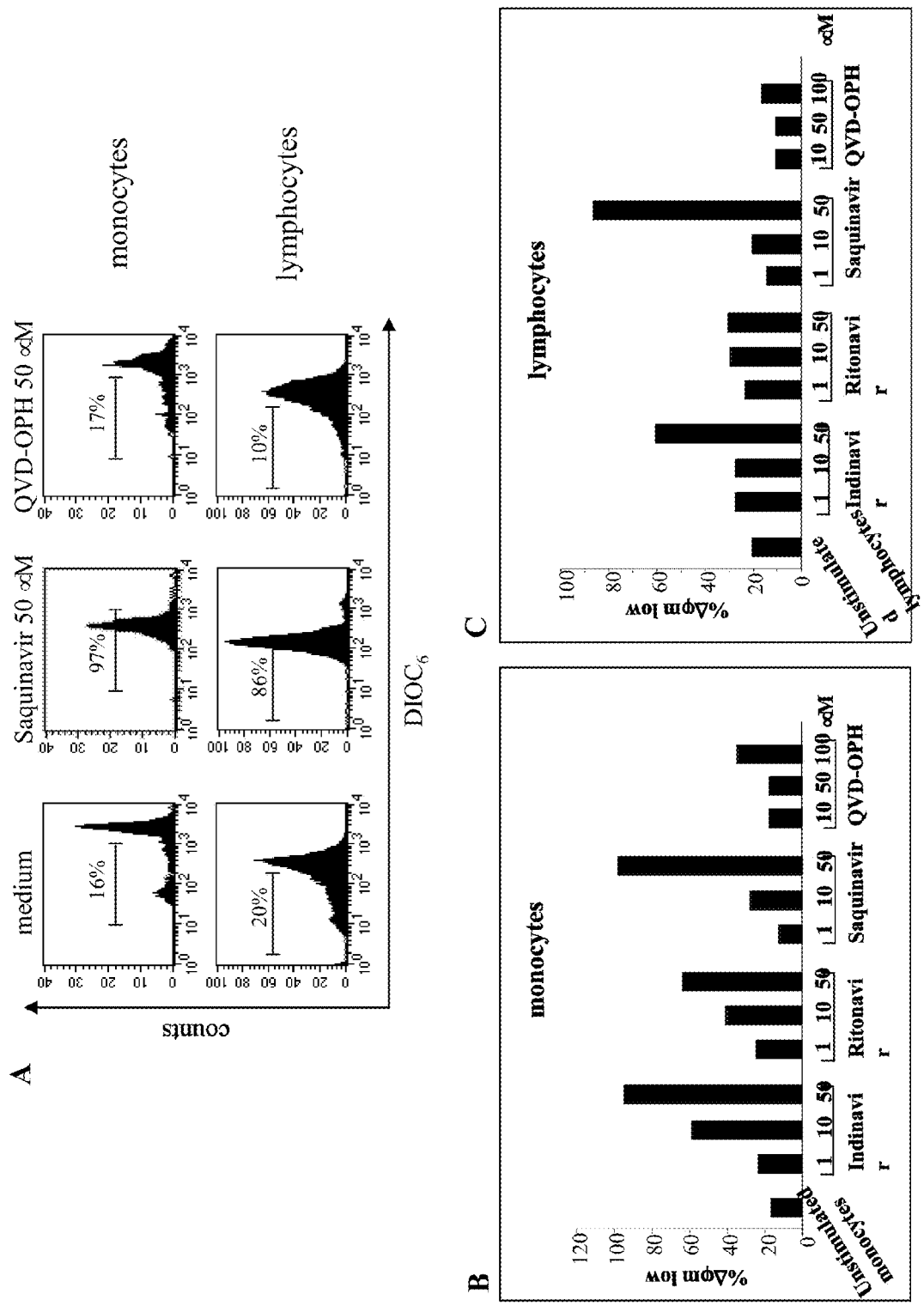

FIG. 15. Analysis of the fall in the mitochondrial transmembrane potential (% Δϕm low) by flow cytometry in monocytes and lymphocytes in the presence of different HIV antiproteases or of QVD-OPH.

EXAMPLES

Example 1

Analysis of the Properties of Q-VD-OPH

A. Material and Methods
Antibodies

For the Immunoblots (Western Blot): anti-Smac/Diablo rabbit polyclonal antibodies (ΨProSci), anti-endonuclease-G (ΨProSci), anticaspase-3 (Stressgen), antiactin (Sigma), anticaspase-8 monoclonal antibodies (Cell Signaling), anti-Cytochrome c clone 7H78.2C12 (BD Pharmingen), anti-Cox IV, subunit IV, clone 10G8 (Molecular Probes).

For cytofluorometry: anti-p24 monoclonal antibody, clone KC57-RD1 (Beckman coulter).
Synthetic Inhibitors Cathepsin D inhibitor: pepstatin A (Sigma).

Broad-spectrum caspase inhibitor: Q-VD-OPh in non-O-methylated form (N-(2-quinolyl)valyl-aspartyl-(2,6-difluorophenoxy)methyl ketone; Enzyme System Products, MP Biomedicals.

Reverse transcriptase inhibitor: didanosine (or ddI) or Videx EC® (Bristol-Myers Squibb).
Isolation of CD4$^+$ Cells and Culture Conditions Peripheral blood mononuclear cells obtained from healthy volunteers (Etablissement Français du sang) were isolated on Ficoll strains (Petit et al., 2002). The majority of the adherent cells were eliminated by incubation in plastics culture dishes. The circulating CD4$^+$ cells were selected negatively using a CD4$^+$ cell isolation kit, in accordance with the supplier's instructions (MACS, CD4 T cell isolation kit II; Miltenyi Biotech, Paris, France). The purity of the isolated CD4$^+$ population, determined by flow cytometry, was ≥96%. Monocytes recovered from the adherent dishes were added to the purified CD4$^+$ cells in a final percentage of 6%. The composition of the culture medium used is as follows: RPMI 1640, 10% foetal calf serum, 2 mM glutamine, 1 mM pyruvate, 50 units/ml of penicillin and 50 μg/mlof streptomycin.
Measurement of Viral Replication The CD4$^+$ cells were incubated for 2 hours at 37° C. in the presence of 10 ng/ml of HIV-1 virus of strain Lai or 50 ng/ml of primary strains of the HIV-1 virus. After 2 washings, the cells were resuspended in a complete medium in the presence of 5 μg/ml of concanavalin A (Con A) and 10 mg/ml of interleukin 2 (IL 2). The HIV p24 antigen, the control for the viral load, was measured in the cell culture supernatants by an ELISA test (Abbott). The intracellular p24 antigen was determined by flow cytometry with the aid of a specific antibody (KC57, Coulter Corp) and after permeabilization of the cells using the permeabilization reagent Intraprep (Coulter Corp.).
Measurement of Cell Death and Analysis by Flow Cytometry In order to evaluate the change in the transmembrane potential of the inner mitochondrial membrane (Δϕm), the CD4$^+$ cells were labelled for 15 minutes at 37° C. with 40 nM of DIOC$_6$ (3-3'-diethyloxacarbocyanine). The dead cells exhibit a reduction in labelling intensity. The size and morphometry were also determined. The apoptotic/dead cells were counted by white-light microscopy, on the basis of abnormal cell morphology and/or the absorption of trypan blue.
Immunoblot (Western Blot)

20 μg extracts of each of the cytosol and mitochondrial fractions were boiled for 5 minutes in Laemmli buffer containing 2% SDS and 10% 2-β-mercaptoethanol and then migrated onto 10-20% polyacrylamide gradient gels (Bio-Rad). After transfer of the proteins to a polyvinylidene difluoride membrane (Bio-Rad), the immunoblots were incubated with the primary and post-secondary antibodies coupled to horseradish peroxidase, obtained from Amersham Biosciences (Orsay, France). They were subsequently developed and revealed by chemiluminescence (ECL from Amersham or West Femto from Pierce) using a CCD camera (Fuji LAS-1000plus) and L process software from Science Lab (Isochem, Paris, France).
Subcellular Fractionation The cytosol and mitochondrial fractions were obtained by the subcellular fractionation technique based on selective permeabilization by digitonin according to Foghsgaard et al. {Foghsgaard, 2001}. Briefly, 10$^7$ cells were washed twice in PBS and incubated for 5 minutes on ice with 100 μl of extraction buffer (35 μg/ml digitonin, 250 mM sucrose, 137 mM NaCl, 70 mM KCl, 4.3 mM Na$_2$HPO$_4$, 1.4 mM KH$_2$PO$_4$, 2 mM EDTA, pH 7.2) supplemented with a protease inhibitor cocktail ("Complete" from Roche Applied Science, Penzberg, Germany). The extracts were centrifuged at 300 g for 5 minutes, and the resulting supernatant was recentrifuged again at 10,000 g for 10 minutes at 4° C. in order to remove the debris. The final supernatant, called the cytosol fraction, was stored at −80° C. The pellet was dissolved in 100 μl of mitochondrial lysis buffer (50 mM Tris pH 7.4, 150 mM NaCl, 2.5 mM EDTA, 2.5 mM EGTA, 0.5% NP40, 0.2% Triton X100) supplemented with "Complete" protease inhibitor cocktail from Roche, for 30 minutes on ice at 4° C., followed by centrifugation at 10,000 g for 30 minutes at 4° C. in order to obtain the so-called "soluble" mitochondrial fraction. The protein concentration of the cytosol and mitochondrial fractions was determined by the bicinchoninic acid (BCA) method (Bio-Rad).
B. Results
B-1. Q-VD-OPh Inhibits Activation of Caspases-3 and -8.

The effectiveness of Q-VD-OPh in inhibiting activation of caspase-3 and -8 was analyzed by immunoblot (Western blot). CD4$^+$ T lymphocytes in culture were infected by the HIV-1 virus and then stimulated, 2 hours after infection, by Concanavalin A and IL-2. Following stimulation, 10 μM of inhibitor Q-VD-OPh were added to the cell culture. Q-VD-OPh was added again 36 hours (3 days) and then 96 hours (4 days) after infection, still at a final concentration of 10 μM. Protein extraction and immunoblot were carried out on the 6th day post-infection.

The results obtained (see FIG. 1) show that, in the absence of viral infection, caspase-3 and -8 are substantially in forms p32 and p55, respectively, which correspond to the inactive forms (proforms) of caspase-3 and -8. The intermediate forms p20 for caspase-3 and p44, p26 and p20 for caspase-8 are also found (Alam et al., 1999; Petit et al., 2002).

When the CD4+ cells were infected by HIV-1 and then cultivated in the absence of inhibitor Q-VD-OPh, it is found, on the 6th day post-infection, that the proforms p32 and p55 are detected only weakly, while the intermediate forms are present in a larger amount. Moreover, the presence of forms p17 and p18, which correspond to the active forms (apoptogenic forms) of caspase-3 and -8, respectively, is detected. This reflects the activation of caspase-3 and -8 by proteolysis following the viral infection.

When the CD4+ cells were infected by the HIV-1 virus and cultivated in the presence of the inhibitor Q-VD-OPh, inhibition of the proteolytic degradation of caspase-3 and -8 is observed; the active forms p17 and p18 are not detected, while the intermediate forms and the proforms p32 and p55 are detected much more strongly than when no inhibitor is administered to the cells infected by HIV. Consequently, the use of the inhibitor Q-VD-OPh has the effect of inhibiting the proteolytic degradation of the proforms of caspase-3 and -8 and accordingly of blocking the activation of caspase-3 and -8.

B-2. Q-VD-OPh inhibits cell death caused by HIV-1 infection.

The inventors evaluated the effect of the compound Q-VD-OPh on cell death caused by HIV-1 infection and on viral replication by analyzing CD4+ T cells infected by the HIV-1 virus and then stimulated by Concanavalin A and IL-2 and incubated or not incubated in the presence of Q-VD-OPh for 5 days (FIG. 2). Analysis of the size and granulometry of the CD4+ T cells (FIG. 2A) as well as the percentage of CD4+ cells exhibiting mitochondrial depolarization, which is characteristic of cell death (FIG. 2B), shows that HIV-1 infection is accompanied by a pronounced increase in cell death of the CD4+ T cells (63.1% compared with 13.3% for the untreated cells). On the other hand, when the CD4+ T cells were incubated with the inhibitor Q-VD-OPh after having been infected by HIV-1, only a slight increase in cell death of the CD4+ T cells is observed (19.8% as compared with 13.3% for the untreated cells). These results show that Q-VD-OPh is a potent inhibitor of cell death resulting from HIV-1 infection, unlike other broad-spectrum caspase inhibitors, such as zVAD-kmk, which prevents the apoptotic phenotype (condensation and fragmentation of the nuclear chromatin) in cells infected by HIV but does not prevent either mitochondrial depolarization or cell death (Petit et al., 2002).

B-3. Q-VD-OPh Inhibits Apoptogenic Mitochondrial Damage Caused by Viral Replication.

The inventors analyzed, by immunotransfer (Western blot), the effect of Q-VD-OPh on the release of apoptogenic mitochondrial factors caused by viral replication. Primary CD4+ T cells were infected with the HIV-Lai virus and then stimulated with a concanavalin NIL-2 cocktail before being treated with Q-VD-OPh (10 µM) and/or pepstatin A (10 µM). On day 5 after infection, the cells were fractionated into two parts: (i) the mitochondrial membrane fraction and (ii) the cytosol fraction, which may contain mitochondrial factors released following permeabilization of the mitochondrial membrane caused by the viral infection.

Analysis of the location of the apoptogenic factors Cytochrome C, Smac/Diablo and Endonuclease G (EndoG) (FIG. 3) shows the presence of these apoptogenic factors in the cytosol fraction of the cells infected by HIV-Lai, whereas in the uninfected cells they are located in the mitochondrial membrane fraction, which is the indicator of mitochondrial damage. This suggests that the massive death of the CD4+ T cells observed following an HIV infection is the result of a mechanism of cell death which passes through a loss of permeability of the mitochondrial membrane and a spreading of apoptogenic factors into the cytosol.

In addition, while the use of pepstatin A appears to have no effect after 5 days on the mitochondrial damage caused by the viral infection, the use of Q-VD-OPh enables the presence of the apoptogenic factors Cytochrome C, Smac/Diablo and EndoG in the cytosol fraction to be reduced very considerably; the presence of Cytochrome C is even almost zero. These results show that Q-VD-OPh allows the mitochondrial damage caused by viral replication to be reduced considerably.

B-4. Q-VD-OPh Inhibits Replication of the HIV-1 Virus.

In order to determine the effect of the compound Q-VD-OPh on viral replication, the replication of the HIV-1 virus in the presence or absence of Q-VD-OPh was evaluated by quantification of the number of TCD4+ lymphocytes expressing the p24 antigen in CD4+ T lymphocytes infected by HIV and stimulated by ConA and IL-2. Analysis of the percentage of CD4+ T lymphocytes infected by HIV-1 on the 5th and 6th days post-infection (FIGS. 2C and 4A, respectively) and of the amount of the p24 viral antigen in the culture supernatants on the 6th day post-infection (FIG. 4B) show that the compound Q-VD-OPh reduces viral replication by more than 75%. The inhibition of viral replication is even stronger when the CD4+ T lymphocytes are treated both with the compound Q-VD-OPh and with another protease inhibitor, pepstatin A (pepsin inhibitor).

FIGS. 2C and 4A show the count of cells expressing the p24 viral antigen by immunological labelling and flow cytometry. Five days after infection, 72.6% of the cells express the viral antigen and are therefore infected. If the infection is followed by the addition of Q-VD-OPh, only 18% of the cells are infected five days after infection.

B-5. The Inhibitory Effect of Q-VD-OPh on Cell Death Caused by Viral Infection and on Viral Replication is Stronger, the Earlier it is Administered.

In order to determine if the time at which the compound O-VD-OPh is administered has an impact on the inhibition of cell death caused by HIV-1 infection and on the inhibition of viral replication, Q-VD-OPh was administered to CD4+ T lymphocytes in culture either before infection with HIV-1 or after. In each case there was determined, by flow cytometry, on the 5th day post-infection, the percentage of CD4+ T lymphocytes infected by the virus by intracellular labelling of the p24 antigen (FIG. 7A) and the percentage of dead CD4+ lymphocytes (FIG. 7B).

The results obtained using increasing concentrations of Q-VD-OPh (0.5; 1; 2; 5; 10 and 20 µM) administered to the CD4+ T lymphocytes after infection by HIV-1 show that the inhibition of viral replication and the inhibition of cell death caused by the viral infection are dose-dependent.

The fact that a high concentration of inhibitor (20 µM) is accompanied by pronounced inhibition of cell death in response to the viral infection also emphasizes the fact that the inhibitor Q-VD-OPh is not only absolutely non-toxic for CD4+ T cells but, on the contrary, promotes survival of CD4+ T cells infected by the HIV-1 virus. Moreover, it is possible that Q-VD-OPh blocks the death of uninfected CD4+ cells (bystander effect; Hurtrel et al., 2005).

Furthermore, when Q-VD-OPh is added before infection by HIV-1 (at a final concentration of 10 µM), inhibition of viral replication and inhibition of cell death are even greater than when Q-VD-OPh is added before infection by HIV-1 (in a concentration of from 0.5 to 20 µM). This shows that the effect of the inhibitor Q-VD-OPh on the viral infection and on the consequences of the viral infection is greater, the earlier it is administered. Accordingly, the inhibitor Q-VD-OPh may be used not only to treat a viral infection but also prophylactically, in order to prevent a viral infection.

B-6. Q-VD-OPh Inhibits the Expression of a Group of HIV-1 Proteins in Primary CD4+ T Cells.

The inventors analyzed the expression, on the 6th day post-infection, of the HIV-1 proteins in the cytosol fractions, the soluble membrane fractions and the insoluble membrane fractions of CD4+ T lymphocytes infected by the HIV-1 virus and then incubated in the presence or absence of the compound Q-VD-OPh. The expression profile obtained (see. FIG. 6) shows that the inhibitor Q-VD-OPh drastically reduces the totality of HIV proteins expressed in the cytosol and in the membrane fractions of the primary CD4+ T lymphocytes. On the other hand, the presence of inhibitors does not cause different compartmentalization of the proteins nor an accumulation of the proforms. Q-VD-OPh therefore has an inhibitory effect for the expression of the totality of the viral genome but has no effect on intracellular protein traffic and therefore on the maturation of the proteins.

B-7. Q-VD-OPh Inhibits the Replication of Primary HIV-1 Strains.

Viral replication was analyzed by flow cytometry in CD4+ T lymphocytes infected by the HIV-1 Lai virus or with the serum of a chronic HIV+ patient containing a primary strain with X4/R5 dual tropism.

In the case of the HIV-1 Lai virus, as in the case of the serum of a chronic HIV+ patient, it is noted that, when the lymphocytes infected by the virus were cultivated in the presence of the compound Q-VD-OPh, viral replication is strongly inhibited (FIG. 5A). 3.79% of infected cells treated with Q-VD-OPh, as compared with 36.46% of the cells not treated with Q-VD-OPh in the case of an infection by the strain LAI and 0.06% of infected cells treated with Q-VD-OPh in the case of an infection by a primary strain.

Moreover, a quantitative analysis of cell death by measurement of mitochondrial depolarization, and of viral replication by ELISA assay of the p24 viral antigen in CD4+ T lymphocytes infected with the serum of the chronic HIV+ patient show that Q-VD-OPh also causes strong inhibition of cell death (total or almost total inhibition) and of viral replication (FIG. 5B) on a primary isolate of the HIV-1 retrovirus.

The inventors further analyzed the replication of five primary HIV-1 isolates taken from HIV+ patients, of R5 tropism, in the absence or presence of the inhibitor Q-VD-OPh or of ddI, a reverse transcriptase inhibitor. It is noted that, for the five primary isolates, Q-VD-OPh and ddI have a similar effect, namely strong inhibition of viral replication (see FIG. 5C). The viral strains with R5 tropism are those which are found most commonly and have the characteristic of emerging early during the infection and of persisting throughout the evolution of the disease, whereas the viral strains with X4 tropism tend to be late strains. The ability of Q-VD-OPh to inhibit viral replication more particularly of the viral strains with R5 tropism renders this molecule very interesting from a therapeutic point of view because it may be used to stop a viral infection at a very early stage.

B-8. Q-VD-OPh Inhibits Replication of the SIVmac251 Virus and the Formation of Syncytia.

In order to evaluate the field of application of the antiviral properties of the inhibitor Q-VD-OPh, the inventors analyzed the effect of Q-VD-OPh on replication of the SIVmac251 virus and on the formation of syncytia (FIG. 8). The cell line CEMx174 was infected with a strong dose of virus of the strain SIVmac251 (200 AID50), which corresponds to ten times the concentration used to infect monkeys. Analysis of viral production in the culture supernatant by RT-PCR on the 4th and 5th days post-infection shows that replication of the SIVmac251 virus is inhibited in the presence of the inhibitor Q-VD-OPh, in a dose-dependent manner. Moreover, when a high concentration of inhibitor (20 µM) is administered, viral replication is inhibited by more than 70%. Consequently, it appears that Q-VD-OPh inhibits replication of the HIV and SIV viruses in a similar manner.

In addition, the formation of syncytia, a characteristic which would be linked to greater or lesser virulence, is likewise strongly inhibited under the effect of the inhibitor Q-VD-OPh. However, a concentration of Q-VD-OPh equal to or greater than 10 µM is required to obtain a 70% reduction in the number of syncytia 5 days after infection and treatment.

These results show that Q-VD-OPh is a broad-spectrum viral replication inhibitor which allows not only HIV viruses but also SIV viruses to be blocked.

B-9. Q-VD-OPh Acts in Synergy with AZT and Indinavir to Inhibit Viral Replication and Death of the CD4+ T Lymphocytes.

The inventors tested the hypothesis according to which the inhibitor Q-VD-OPh might have a synergistic effect with other antiviral molecules used in combating HIV, in particular with azidothymidine (AZT), a reverse transcriptase inhibitor, and with Indinavir, a protease inhibitor. Primary CD4+ T cells were infected by an HIV-Lai virus and then stimulated with concanavalin A and IL-2. The cells were then cultivated in the presence or absence of Q-VD-OPh (0.1, 1 or 10 µM) and in the presence or absence of AZT (0.1 µM) or Indinavir (1 µM). Where the drugs were added to the culture, they were added 96 hours (d3) after infection. Cell death was then quantified by flow cytometry on the 5th day post-infection.

The results obtained (FIG. 9) show that Q-VD-OPh, when used in combination with AZT or Indinavir, inhibits cell death resulting from viral infection much more strongly than Q-VD-OPh, AZT or Indinavir used alone. Consequently, Q-VD-OPh used in association with anti-HIV treatments for preventing cell death, which is a consequence of viral replication, gives rise to a synergistic effect.

C. Conclusion

The totality of these works clearly shows that the compound Q-VD-OPh is a potent inhibitor of the replication of the HIV and SIV viruses. The more effective inhibitory effect of Q-VD-OPh when administered before infection (pretreatment—see Example B5) shows, moreover, that this molecule acts during the first stages of the replication cycle of the virus. The compound Q-VD-OPh is therefore of major interest for therapeutic use as an antiviral agent and in particular as an antiretroviral agent, and as an antilentiviral agent.

Furthermore, the ability of Q-VD-OPh to prevent apoptosis may be an additional advantage allowing the immune response in respect of pathogenic agents to be restored in a more consistent manner.

It is to be noted that the use of another broad-spectrum caspase inhibitor z-VAD-fmk does not inhibit apoptosis of those cells during viral replication (Petit et al., 2002) nor does it inhibit viral replication of HIV or the death of the T lymphocytes induced by HIV infection (Petit et al., 2002), suggesting that this new inhibitor may have a major role in the fight against this viral infection.

In addition, Q-VD-OPh is capable of acting in synergy with other antiviral molecules such as AZT and Indinavir. The use of Q-VD-OPh in association with other antiviral molecules, in particular with other molecules from the range of anti-HIV agents currently available, therefore appears particularly promising.

Example 2

Comparative Analysis

A. Material and Methods
Analysis by Flow Cytometry of the Fall in λϕm and of the p24 Protein of the HIV Virus In order to evaluate the change in the transmembrane potential of the inner mitochondrial membrane, the cells were labelled with a fluorescent probe $DIOC_6$ (Molecular Probes, Invitrogen), at a concentration of 40 nM, and incubated for 15 minutes at 37° C. Viral replication was evaluated by internal labelling of the p24 viral protein using an anti-p24-PE antibody (KC-57, Coulter Corp, Beckman).

Immunoblot

20 μg extracts of total lysate prepared with 1% NP40 were boiled for 5 minutes in Laemmli buffer containing 2% SDS and 10% 2-β-mercaptoethanol, then deposited on 10-20% polyacrylamide gradient gels (Invitrogen). After transfer of the proteins, the immunoblots were incubated with the following primary antibodies: anticaspase-3, anticaspase-8 and anticaspase-9 (Cell Signaling), anti-PARP (Pharmingen) and anti-Tubulin (Santa-Cruz). The secondary antibodies coupled to peroxidase (horseradish) (Amersham Biosciences) allows the proteins to be revealed by chemiluminescence (ECL, Amersham) using a CCD camera (G: Box-Chemi-XT16-SynGene).

Synthetic Inhibitors and Other Chemical Products

The broad-spectrum caspase inhibitor Z-VAD-fmk (Calbiochem), the general caspase inhibitor: Q-VD-OPH, the caspase-8 inhibitor: Q-IETD-OPH, the caspase-3, -7 inhibitor: Q-DEVD-OPH and the caspase-9 inhibitor: Q-LEHD-OPH (MP Biomédicals, France) were used. The anti-CD95 antibody (human Fas) (clone 7C11, Immunotech) was used to induce apoptosis. The HIV antiproteases Saquinavir, Ritonavir and Indinavir are obtained from NIH. The probe CFSE (carboxyfluorescein diacetate succinimidyl ester) used for the proliferation study was obtained from Molecular Probes (Invitrogen).

Proliferation Test with CFSE

The PBMCs are incubated in the presence of 1 μM of CFSE for 7 minutes at 37° C. The cells are taken up at $1.10^6$/ml and then placed in culture and activated by an anti-CD3 at 1 μg/ml (Immunotech).

B. Results

B-1. Validation of New Caspase Inhibitors

B-1-a. Determination of the Functionality of New Specific Caspase-3, -8 and -9 Inhibitors in Respect of Apoptosis Induced by Fas/CD95.

Jurkat cells were incubated in the presence or absence of anti-CD95 at different concentrations in order to determine a dose-response curve for apoptosis. Death was evaluated by analyzing the fall in the mitochondrial transmembrane potential (% Δϕm low) using the probe DIOC6, by flow cytometry (FIG. 10A). The same experiment was then conducted in the presence of 0.25 μg/ml of anti-CD95 and different caspase inhibitors. The apoptosis induced by anti-CD95 is expressed by the percentage Δϕm low analyzed by flow cytometry (FIG. 10B).

Jurkat cell extracts which have been treated in the presence or absence of anti-CD95 and of the different caspase inhibitors were analyzed by immunoblot for caspase-3, -8, -9 and PARP (substrate specific to caspase-3 and -7), tubulin is used as control for the deposits (FIG. 10C).

B-1-b. Determination of the Ability of the Specific Inhibitors to Inhibit Viral Replication and Consequently Cell Death.

Primary CD4 T cells were infected by the viral strain HIV-Lai and then stimulated by ConA/IL-2 in the presence or absence of Q-VD-OPH, Q-DEVD-OPH (casp-3 inhibitor), Q-LEDH-OPH (caspase-9 inhibitor) and Q-IETD-OPH (caspase-8 inhibitor) at 10 μM for each of the inhibitors. On days 5 and 7 post-infection, the internal p24 viral protein is measured by flow cytometry after fixation and permeabilization of the CD4 T cells. The results show a weak effect on inhibition of viral replication for each of the different specific caspase inhibitors on d5 and an absence of protection at d7; Q-VD-OPH, on the other hand, inhibits replication completely (FIG. 11A). Death was evaluated by analysis of the fall in the mitochondrial transmembrane potential (% Δϕm low) using the probe DIOC6 by flow cytometry (FIG. 11B). We show an absence of effect of these inhibitors, contrary to Q-VD-OPH. Extracts of primary CD4 T cells infected in the presence or absence of the different caspase inhibitors as well as QVD-OPH were analyzed by immunoblot for the HIV viral proteins (FIG. 12). The results show that the quantity of viral proteins produced in the presence of the different inhibitors is slightly lower than that of the control cultures, but that viral production is very markedly reduced in the presence of QVD-OPH. These results are in agreement with our observations regarding the detection of the p24 protein by flow cytometry.

B-2. Toxic Effects of the Drugs

B-2-a. QVD-OPH at 50 μM does not Block the Proliferation of Lymphocytes Stimulated by 1 μg/ml of anti-CD-3.

A lymphocyte proliferation study was conducted with the fluorescent probe CFSE, which allows cell division to be monitored. The PBMCs are stimulated with anti-CD3 at 1 μg/ml and incubated in the presence or absence of the HIV antiproteases Saquinavir, Ritonavir and Indinavir, at concentrations of 1 μM, 10 μM and 50 μM, as well as QVD-OPH at 10 μM, 50 μM and 100 μM. Analysis of CFSE carried out after 4 and 5 days' stimulation shows, by flow cytometry, that the HIV antiproteases block the proliferation of lymphocytes at a dose of 50 μM. QVD-OPH, on the other hand, at the same concentrations, has no effect on lymphocyte proliferation (FIG. 13).

The cell toxicity was evaluated by analysis of the fall in the mitochondrial transmembrane potential (% Δϕm low) using the probe DIOC6, by flow cytometry. The cells stimulated by anti-CD3 were analyzed in the same way on the day following activation. Accordingly, QVD-OPH, even at high concentrations (100 μM), has no effect on mitochondrial depolarization (compared with the control), whereas Indinavir and Saquinavir show a fall in Δϕm of more than 70-80% at a dose of 50 μM (FIG. 14).

B-2-b. Evaluation of the Toxicity of QVD-OPH in Respect of Lymphocytes and Monocytes.

PBMCs are incubated in the presence of the different HIV antiproteases Saquinavir, Ritonavir and Indinavir, at concentrations of 1 μM, 10 μM and 50 μM, as well as QVD-OPH at 10 μM, 50 μM and 100 μM. The cell toxicity was evaluated by analysis of the fall in the mitochondrial transmembrane potential (% Δϕm low) after 4 days' culture by analyzing the monocytes and lymphocytes. The effect of QVD-OPH on mitochondrial depolarization remains minimal on one or other of the populations even at a concentration of 100 μM, while the HIV antiproteases, in particular Saquinavir, show depolarization of more than 90% (FIGS. 15A and B). These results are in agreement with our previous works.

BIBLIOGRAPHY

The following articles are incorporated by reference in their entirety:

Alam et al. (1999). J. Exp. Med. 190(12): 1879-1890.
Amendola et al. (1996). Proc Natl Acad Sci USA. 93(20): 11057-62.
Barber (2001). Cell Death and Diff. 8: 113-126.
Caserta et al. (2003). Apoptosis. 8(4): 345-52.

Chinnaiyan et al. (1997). Nature Medicine. 3(3): 333-337.
Cryns et al. (1998). Genes & Development 12: 1551-1570.
Everett & McFadden. (1999). Trends in Microbiology. 7: 160-165.
Finkel et al. (1995). Nat. Med. 1(2): 129-34.
Gandhi et al. (1998). The Journal of Experimental Medecine. 187(7): 1113-1122.
Gordon et al. (2005). The call of the wild: what can be learned from studies of SIV infection of natural hosts? In Leitner T, Foley B, Hahn B, Marx P, McCutchan F, Mellors J, Wolinsky S, and Korber B (eds.). HIV Sequence Compendium, 2005. Theoretical Biology and Biophysics Group, Los Alamos National Laboratory, NM, LA-UR 04-7420. 2-29
Gougeon et al. (1996), J Immunol. 156(9): 3509-20.
Hurtrel at al. (2005). Cell Death Differ. 12: 979.
Lavrik et al. (2005). The Journal of Clinical Investigation. 115(10): 2665-2672.
Levine at al. (1996). Proc Natl Acad. Sci. 93: 4810.
Liang et al. (1998). J Virol. 72: 8586.
Olsen et al. (1996). J Virol. 70: 663.
Petit at al. (2002). J Biol. Chem. 277: 1477.
Sticht at al. (2005). Nat Struct Mol Biol. 12: 671.
Ternois et al. (2005). Nat Struct Mol Biol. 12: 678.
Thornberry and Labzebnik (1998). Science. 281: 1312.
Vera et al. (2005). Biology of Reproduction. 72: 516-522.
Wurzer et al. (2003). EMBO J. 22: 2717.

What is claimed is:

1. A method for the treatment of an animal or human infected by a human immunodeficiency virus (HIV), comprising administration to an animal or human in need thereof a Q-VD-Oph compound selected from the group consisting of N-(2-quinolyl)valyl-O-methyl-aspartyl-(2,6-difluorophenoxy)methyl ketone and N-(2-quinolyl)valyl-aspartyl-(2,6-difluorophenoxy)methyl ketone.

2. The method according to claim 1, in which said human immunodeficiency virus is HIV-1 or HIV-2.

3. The method according to claim 2, in which said human immunodeficiency virus is HIV-1.

4. The method according to claim 1, in which said animal or human has acquired immunodeficiency syndrome (AIDS).

5. The method according to claim 1, in which said animal is a non-human mammal.

6. The method according to claim 5, in which said non-human mammal is an ape or a cat.

7. The method according to claim 1, further comprising the administration of one or more carrier(s), diluent(s) or adjuvant(s) or a combination thereof.

8. The method according to claim 1, comprising administering the compound by a route selected from the group consisting of the enteral, parenteral, transcutaneous, cutaneous, oral, mucosal, transmucous-buccal, nasal, ophthalmological, otological, vaginal, rectal, intragastric, intracardiac, intraperitoneal, intrapulmonary and intratracheal routes.

9. The method according to claim 1, comprising administering the compound to said animal or human during exposure to the virus and/or after exposure to the virus.

10. The method according to claim 1, comprising administering the compound several times in succession.

11. The method according to claim 1, comprising the separate, simultaneous or sequential administration of a combination comprising:
(i) at least a Q-VD-OPh compound selected from the group consisting of N-(2-quinolyl)valyl-O-methyl-aspartyl-(2,6-difluorophenoxy)methyl ketone and N-(2quinolyl)valyl-aspartyl-(2,6-difluorophenoxy)methyl ketone; and
(ii) at least one other antiviral agent.

12. The method according to claim 11, wherein compounds (i) and (ii) are present in two distinct compositions.

13. The method according to claim 12, wherein the composition comprising compound (i) and/or the composition comprising compound (ii) further comprises one or more carrier(s), diluent(s) or adjuvant(s) or a combination thereof.

14. The method according to claim 11, wherein said other antiviral agent is selected from the group consisting of:
transcriptase inhibitors;
viral protease inhibitors or antiproteases;
inhibitors of the fusion of the viral envelope with the cell membrane;
receptor or coreceptor inhibitors;
antisense oligonucleotides;
integrase inhibitors; and
molecules that target other steps of viral multiplication.

15. The method according to claim 11, wherein said other antiviral agent or at least one of said other antiviral agents comprises at least one transcriptase inhibitor and/or at least one viral protease inhibitor.

16. The method according to claim 15, wherein said transcriptase inhibitor is a reverse transcriptase inhibitor.

17. The method according to claim 15, wherein said transcriptase inhibitor is HIV virus reverse transcriptase inhibitor.

18. The method according to claim 16, wherein the reverse transcriptase inhibitor is selected from the group consisting of zidovudine or azidothymidine (AZT), didanosine or ddI, zalcitabine or ddC, stavudine or d4T, lamivudine or 3TC, abacavir or ABC, emtricitabine or FTC, nevirapine, efavirenz, delavirdine and tenofovir or bis-POC-PMPA.

19. The method according to claim 16, wherein the reverse transcriptase inhibitor is AZT.

20. The method according to claim 15, wherein the viral protease inhibitor is an HIV virus protease inhibitor.

21. The method according to claim 15, wherein the viral protease inhibitor is selected from the group consisting of Indinavir or IDV, Nelfinavir or NLFN, Saquinavir or SQN, Ritonavir or RTN, Amprenavir and Lopinavir.

22. The method according to claim 15, wherein the viral protease inhibitor is Indinavir.

23. The method according to claim 11, comprising administering the compounds (i) and (ii) by a route selected from the group consisting of the enteral, parenteral, transcutaneous, cutaneous, oral, mucosal, buccal, nasal, oesophageal, vaginal, rectal, intragastric, intracardiac, intraperitoneal, intrapulmonary and intratracheal routes.

24. The method according to claim 11, wherein said animal is a non-human mammal.

25. The method according to claim 24, wherein said non-human mammal is an ape or a cat.

26. The method according to claim 9, comprising administering the compound to an animal or human within 48 hours of said animal or human being exposed to said virus.

27. The method according to claim 11, wherein the other antiviral agent is an antiretroviral agent.

28. A method for delaying the appearance of clinical signs or symptoms of human immunodeficiency virus (HIV) infection, comprising administering to an animal or human in need thereof at or after the time of exposure to HIV, a Q-VD-Oph compound selected from the group consisting of N-(2-quinolyl)valyl-O-methyl-aspartyl-(2,6-difluorophenoxy) methyl ketone and N-(2-quinolyl)valyl-aspartyl-(2,6-difluorophenyoxy) methyl ketone.

* * * * *